(12) United States Patent
Cunningham et al.

(10) Patent No.: US 12,351,780 B2
(45) Date of Patent: Jul. 8, 2025

(54) PEPTIDE ACETALS FOR STABILISING ENZYMES

(71) Applicant: BASF SE, Ludwigshafen (DE)

(72) Inventors: Allan F. Cunningham, Basel (CH); Stefan Jenewein, Ludwigshafen (DE); Gabriele Boenemann, Basel (CH)

(73) Assignee: BASF SE, Ludwigshafen am Rhein (DE)

( * ) Notice: Subject to any disclaimer, the term of this patent is extended or adjusted under 35 U.S.C. 154(b) by 697 days.

(21) Appl. No.: 17/621,807

(22) PCT Filed: Jun. 24, 2020

(86) PCT No.: PCT/EP2020/067722
§ 371 (c)(1),
(2) Date: Dec. 22, 2021

(87) PCT Pub. No.: WO2021/001244
PCT Pub. Date: Jan. 7, 2021

(65) Prior Publication Data
US 2022/0267699 A1    Aug. 25, 2022

(30) Foreign Application Priority Data
Jul. 1, 2019  (EP) .................................... 19183669

(51) Int. Cl.
| | | |
|---|---|---|
| *C11D 3/32* | (2006.01) | |
| *C07K 1/107* | (2006.01) | |
| *C07K 5/083* | (2006.01) | |
| *C07K 5/09* | (2006.01) | |
| *C07K 5/097* | (2006.01) | |
| *C11D 3/386* | (2006.01) | |

(52) U.S. Cl.
CPC .............. *C11D 3/32* (2013.01); *C07K 1/1075* (2013.01); *C07K 5/0806* (2013.01); *C07K 5/0808* (2013.01); *C07K 5/0817* (2013.01); *C07K 5/0821* (2013.01); *C11D 3/386* (2013.01)

(58) Field of Classification Search
CPC ........ C11D 3/32; C11D 3/386; C07K 1/1075; C07K 5/0806; C07K 5/0808; C07K 5/0817; C07K 5/0821
See application file for complete search history.

(56) References Cited

U.S. PATENT DOCUMENTS

| | | | |
|---|---|---|---|
| 4,478,745 A | 10/1984 | Bajusz et al. | |
| 4,623,639 A | 11/1986 | Hassall et al. | |
| 4,691,007 A | 9/1987 | Dutta et al. | |
| 4,703,036 A | 10/1987 | Bajusz et al. | |
| 4,708,944 A | 11/1987 | Someno et al. | |
| 4,742,081 A | 5/1988 | Stracher et al. | |
| 4,880,780 A | 11/1989 | Trainor et al. | |
| 5,436,229 A | 7/1995 | Ruterbories et al. | |
| 5,508,385 A | 4/1996 | Abe et al. | |
| 5,578,574 A | 11/1996 | Shuman et al. | |
| 6,500,802 B1 | 12/2002 | Tao et al. | |

FOREIGN PATENT DOCUMENTS

| | | |
|---|---|---|
| EP | 1921147 A2 | 5/2008 |
| WO | WO-94/04651 A1 | 3/1994 |
| WO | WO-95/25791 A1 | 9/1995 |
| WO | WO-96/30395 A2 | 10/1996 |
| WO | WO-98/13458 A1 | 4/1998 |
| WO | WO-98/13460 A1 | 4/1998 |
| WO | WO-98/47523 A1 | 10/1998 |
| WO | WO-2009/118375 A2 | 10/2009 |
| WO | WO-2011/036153 A1 | 3/2011 |
| WO | WO-2013/004636 A1 | 1/2013 |

OTHER PUBLICATIONS

Harer, et al., "Proteasome inhibitors mechanism; source for design of newer therapeutic agents", The Journal Of Antibiotics, vol. 65, Issue 8, Apr. 18, 2012, pp. 279-288.
Bringmann, et al., A Simple, Chiral-Pool-Independent Synthesis of Enantiomerically Pure Alanine-Derived α-Amino Aldehyde Acetals, Synthesis, Issue 8, 1989, pp. 608-610.
European Search Report for EP Patent Application No. 19183669.1, Issued on Jan. 7, 2020, 6 pages.
Grobelny et al., Aldehyde and ketone substrate analogues inhibit the collagenase of Clostridium histolyticum, Biochemistry, 24(22):6145-52 (1985).
International Application No. PCT/EP2020/067722, International Search Report and Written Opinion, mailed Sep. 9, 2020.
Konno, et al., Synthetic study of peptide aldehyde via acetal/thioacetal transformation: application for Lys/Ser-containing peptides, Tetrahedron, vol. 71, Issue 21, May 27, 2015, pp. 3433-3438.
Nomoto et al., Syntheses of capreomycin analogs in relation to their antibacterial activities, Bulletin of the Chemical Society of Japan, 52(6):1709-15 (1979).
Someno et al., A simple method for semi-synthesis of peptidyl argininals as potent inhibitors of trypsin-like proteases, Chem. Pharm. Bull., 34(4):1748-54 (1986).
Teshima et al., Chemical studies on tuberactinomycin. XIII. Syntheses and antimicrobial activities of [Ala 3, Ala 4]-, [Ala 3]-, and [Ala 4]-tuberactinomycin O, Bulletin of the Chemical Society of Japan, 50(12):3372-80 (1977).

*Primary Examiner* — Li N Komatsu
(74) *Attorney, Agent, or Firm* — ArentFox Schiff LLP

(57) ABSTRACT

The present invention relates to a compound for stabilizing enzymes, the use of said compound for stabilizing an enzyme, a composition comprising said compound, a method of preparing the composition comprising said compound, a detergent composition comprising said compound and a method of preparing said compound.

19 Claims, No Drawings

Specification includes a Sequence Listing.

SEQUENCE LISTING

<160> NUMBER OF SEQ ID NOS: 1

<210> SEQ ID NO 1
<211> LENGTH: 269
<212> TYPE: PRT
<213> ORGANISM: Bacillus lentus

<400> SEQUENCE: 1

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Glu Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

PEPTIDE ACETALS FOR STABILISING ENZYMES

CROSS-REFERENCE TO RELATED APPLICATIONS

This is the U.S. national phase of International Application No. PCT/EP2020/067722, filed Jun. 24, 2020, which claims priority to European Patent Application No. 19183669.1, filed Jul. 1, 2019.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "180982_Seqlisting.txt", which was created on Dec. 6, 2021 and is 2,638 bytes in size. The subject matter of the Sequence Listing is incorporated herein in its entirety by reference.

The present invention relates to a compound for stabilizing enzymes, the use of said compound for stabilizing an enzyme, a composition comprising said compound, a method of preparing the composition comprising said compound, a detergent composition comprising said compound and a method of preparing said compound.

BACKGROUND OF THE INVENTION

WO 98/13458, WO 94/04651, WO 98/13460, WO 95/25791, and WO 2009/118375 disclose liquid detergents with a subtilisin-type protease stabilized by a peptide aldehyde. WO 2011/036153 discloses that the addition of a peptide aldehyde to a particulate subtilisin-containing detergent can improve the detergency. WO 2013/004636 discloses a composition comprising a subtilisin and a peptide aldehyde hydrosulfite adduct.

WO 98/47523 and U.S. Pat. No. 6,500,802 disclose peptidyl-2-amino-1-hydroxyalkanesulfonic acids and their use as protease inhibitors. U.S. Pat. No. 5,436,229 discloses bisulfite adducts of L-arginine aldehyde derivatives and their use as thrombin inhibitors. US 4,691,007 discloses bisulfite adducts of tetrapeptide aldehydes useful as human leukocyte elastase inhibitors.

U.S. Pat. Nos. 4,703,036, 4,478,745 and 5,578,574 disclose methods of preparing peptide aldehydes in dry form.

However, there is still a need for compounds which efficiently stabilize enzymes.

SUMMARY OF THE INVENTION

Aldehydes, particularly peptide aldehydes, used for enzyme stabilization are prone to inactivation by chemical reactions. The inventors have found that the acetal form of an aldehyde, particularly the acetal form of a peptide aldehyde, is itself effective as an enzyme inhibitor and stabilizer, particularly as a protease inhibitor and stabilizer, and that it can also stabilize a second enzyme, if present. The inventors have found that said acetal is effective as enzyme inhibitor, particularly as protease inhibitor, and that it maintains its inhibitory and stabilizing effect in a liquid detergent during storage. The addition of said acetals may also improve the detergency (wash performance) of a protease-containing detergent, particularly a subtilisin-containing detergent.

Accordingly, the present invention relates to compound of formula (I) or a salt thereof wherein

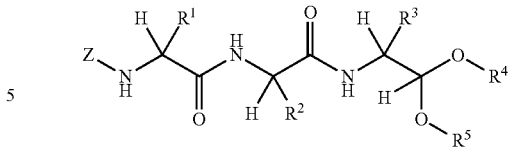

$R^1$, $R^2$ and $R^3$ are each independently selected from the group consisting of hydrogen, optionally substituted $C_{1-8}$ alkyl, optionally substituted $C_{2-6}$ alkenyl, optionally substituted $C_{1-8}$ alkoxy, optionally substituted 3- to 12-membered cycloalkyl, and optionally substituted 6- to 10-membered aryl; or wherein each $R^1$, $R^2$ and $R^3$ is independently selected as —$(CH_2)_3$— which is also attached to the nitrogen atom of —NH—C(H)— so that —N—C(H)$R^{1,2\ or\ 3}$— forms a 5-membered heterocyclic ring;

$R^4$ and $R^5$ are each independently selected from the group consisting of hydrogen, optionally substituted $C_{1-8}$ alkyl, optionally substituted $C_{2-6}$ alkenyl, optionally substituted $C_{1-8}$ alkoxy, optionally substituted $C_{1-4}$acyl, optionally substituted $C_{1-8}$alkyl phenyl, and optionally substituted 6- to 10-membered aryl; or wherein $R^4$ and $R^5$ are joined to form an optionally substituted 5- to 12-membered ring;

Z is selected from hydrogen, an N-terminal protection group, and one or more amino acid residues optionally comprising an N-terminal protection group.

In one embodiment $R^1$ and $R^2$ is a group such that NH—CHR$^1$—CO and NH—CHR$^2$—CO is an L or D-amino acid residue of Gly, Ala, Val, Leu, Ile, Met, Pro, Phe, Trp, Ser, Thr, Asp, Gln, Tyr, Cys, Lys, Arg, His, Asn, Glu, m-tyrosine, 3,4-dihydroxyphenylalanine, Nva, or Nle.

In one embodiment $R^3$ is a group such that NH—CHR$^3$—CO is an L or D-amino acid residue of Gly, Ala, Val, Leu, Ile, Met, Pro, Phe, Trp, Ser, Thr, Asp, Gln, Tyr, Cys, Lys, Arg, His, Asn, Glu, m-tyrosine, 3,4-dihydroxyphenylalanine, Nva, or Nle, or wherein $R^3$ is $(CH_3)_3SiCH_2$.

In one embodiment $R^1$ is a group such that NH—CHR$^1$—CO is an L or D-amino acid residue of Ala, Val, Gly, Arg, Leu, Phe or Thr.

In one embodiment $R^2$ is a group such that NH—CHR$^2$—CO is an L or D-amino acid residue of Ala, Cys, Gly, Pro, Ser, Thr, Val, Nva or Nle.

In one embodiment $R^3$ is a group such that NH—CHR$^3$—CO is an L or D-amino acid residue of Tyr, m-tyrosine, 3,4-dihydroxyphenylalanine, Phe, Val, Ala, Met, Nva, Leu, Ile or Nle.

In one embodiment $R^4$ and $R^5$ are each independently selected from methyl (Me), ethyl (Et), isopropyl (iPr) or isobutyl (iBu), preferably from methyl or ethyl.

In one embodiment $R^4$ and $R^5$ are both methyl, ethyl, or isopropyl.

In one embodiment Z is an N-terminal protection group.

In one embodiment the N-terminal protection group is selected from benzyloxycarbonyl (Cbz), p-methoxybenzyl carbonyl (MOZ), benzyl (Bn), benzoyl (Bz), p-methoxybenzyl (PMB), p-methoxyphenyl (PMP), formyl, acetyl (Ac), methyloxy, alkoxycarbonyl, methoxycarbonyl (Moc), fluorenylmethyloxycarbonyl (Fmoc) or tert-butyloxycarbonyl (t-Boc). The present invention further relates to the use of the compound as disclosed herein for stabilizing an enzyme. In one embodiment the enzyme is a hydrolase, preferably a protease.

The present invention further relates to a composition comprising a compound as disclosed herein and an enzyme, preferably a hydrolase, more preferably a protease. In one embodiment the protease is a serine protease and preferably is a subtilisin protease. In one embodiment the composition further comprises a surfactant. In one embodiment the composition is in liquid or granular form. In one embodiment the composition comprises at least a second enzyme different from the first enzyme, preferably a lipase, protease, cutinase, amylase, carbohydrase, cellulase, pectinase, pectate lyase, mannanase, arabinase, galactanase, xylanase, oxidase, laccase or peroxidase.

The present invention further relates to a method of preparing the composition as disclosed herein comprising the step of mixing the enzyme, preferably the hydrolase, more preferably the protease, the compound of formula (I) as disclosed herein.

The present invention further relates to a detergent composition comprising the compound as disclosed herein or the composition as disclosed herein and optionally a surfactant.

The present invention further relates to a method of preparing a compound of formula (I) comprising the steps:

a) providing a compound according to formula

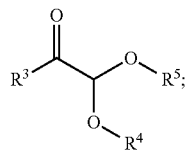

b) converting the compound of step a) to

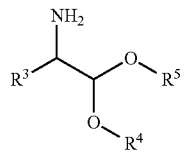

or the corresponding salt thereof having the formula

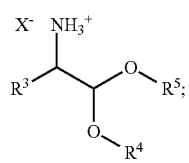

c) reacting the compound or the corresponding salt thereof obtained in step b) with

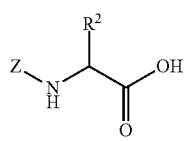

to obtain

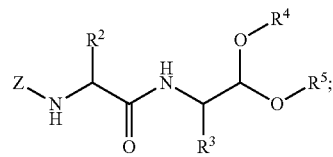

d) optionally, converting the compound obtained in step c) to

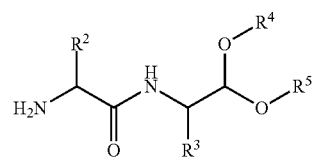

if Z is not hydrogen;

e) reacting the compound obtained in step c) or d) with

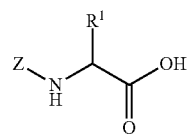

to obtain a compound according to formula (I)

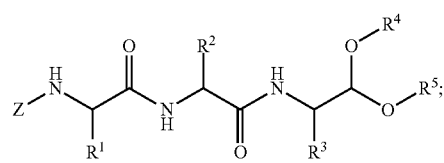

wherein X is selected from F, Cl, Br and I; and
wherein $R^1$ to $R^5$ and Z are as defined herein.

DETAILED DESCRIPTION OF THE INVENTION

Although the present invention will be described with respect to particular embodiments, this description is not to be construed in a limiting sense.

Before describing in detail exemplary embodiments of the present invention, definitions important for understanding the present invention are given. Unless stated otherwise or apparent from the nature of the definition, the definitions apply to all methods and uses described herein.

As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

The term "alkyl" as used by itself or as part of another group refers to a straight- or branched-chain aliphatic hydrocarbon containing one to eight carbon atoms (i.e., $C_{1-8}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-8}$ alkyl group. In another embodiment, the alkyl group is chosen from a branched chain $C_{3-8}$ alkyl group. In another embodiment, the alkyl group is chosen from a straight chain $C_{1-6}$ alkyl group. In another embodiment, the alkyl group is chosen from a branched chain $C_{3-6}$ alkyl group. In another embodiment, the alkyl group is chosen from a straight chain $C_{1-4}$ alkyl group. In another embodiment, the alkyl group is chosen from a branched chain $C_{3-4}$ alkyl group. In another embodiment, the alkyl group is chosen from a straight or branched chain $C_{3-4}$ alkyl group. Non-limiting exemplary $C_{1-8}$ alkyl groups include methyl, ethyl, propyl, isopropyl, butyl, sec-butyl, tert-butyl, iso-butyl, 3-pentyl, hexyl, heptyl, and octyl. Non-limiting exemplary $C_{1-4}$ alkyl groups include methyl, ethyl, propyl, isopropyl, butyl, sec-butyl, tert-butyl, and iso-butyl.

The term "optionally substituted alkyl" as used herein by itself or as part of another group means that the alkyl as defined above is either unsubstituted or substituted with one or more (e.g., one, two, or three) substituents independently selected from the group consisting of amino, (alkyl)amino, (alkyl)carbonyl, (aryl)carbonyl, (alkoxy)carbonyl, [(alkoxy)carbony]amino, carboxy, aryl, heteroaryl, ureido, guanidino, halogen, sulfonamido, hydroxyl, (alkyl)sulfanyl, nitro, haloalkoxy, aryloxy, aralkyloxy, (alkyl)sulfonyl, (cycloalkyl)sulfonyl, (aryl)sulfonyl, cycloalkyl, sulfanyl, caboxamido, heterocyclyl, (heterocyclyl) sulfonyl, amides, (alkyl)phosphates, nitrile, (alkyl)ethers, (alkyl)esters, and silyl, such as alkyl silyl. In one embodiment, the optionally substituted alkyl is substituted with two substituents. In another embodiment, the optionally substituted alkyl is substituted with one substituent. Non-limiting exemplary optionally substituted alkyl groups include $CH(CH_3)CONH_2$, $—CH_2CH_2NO_2$, $—CH(OH)CH_2(OH)$, $—CH(OH)CH(OH)CONH_2$, $—CF_3$, $—CH_2CH_2CO_2H$, $—CH_2Ph-OH$, $—CH_2SH$, $—CH_2CO_2H$, $—CH(CH_3)OH$, $—CH_2CH_2CH_2NC(=NH)NH_2$, $—CH_2CH_2SCH_3$, $—CH_2CH_2COPh$, and $—CH_2C_6H_{11}$.

As used herein, the term "cycloalkyl" by itself or as part of another group refers to saturated or partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is a saturated or unsaturated $C_{3-8}$ cycloalkyl group. In another embodiment, the cycloalkyl group is a saturated or unsaturated $C_{5-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, and cyclohexenyl.

As used herein, the term "optionally substituted cycloalkyl" by itself or as part of another group means that the cycloalkyl as defined above is either unsubstituted or substituted with one, two, or three substituents independently selected from the group consisting of halo, nitro, cyano, hydroxyl, amino, (alkyl)amino, (dialkyl)amino, haloalkyl, (hydroxyl)alkyl, (dihydroxy)alkyl, alkoxy, haloalkoxy, aryloxy, aralkyloxy, alkylthio, carboxamido, sulfonamido, (alkyl)carbonyl, (aryl)carbonyl, (alkyl)sulfonyl, arylsulfonyl, ureido, guanidino, carboxy, (carboxy)alkyl, alkyl, cycloalkyl, alkenyl, alkynyl, aryl, heteroaryl, heterocyclyl, (alkoxy)alkyl, (amino)alkyl, (hydroxyl)alkylamino, (alkylamino)alkyl, (dialkylamino)alkyl, (cyano)alkyl, (carboxamido)alkyl, (alkyl)sulfanyl, (heterocyclo)alkyl, (heteroaryl)alkyl, (alkoxy)carbonyl, mercaptoalkyl, amides, (alkyl)phosphates, nitrile, (alkyl)ethers, (alkyl)esters, and silyl, such as alkyl silyl. In one embodiment, the optionally substituted cycloalkyl is substituted with two substituents. In another embodiment, the optionally substituted cycloalkyl is substituted with one substituent. Non-limiting exemplary optionally substituted cycloalkyl groups include:

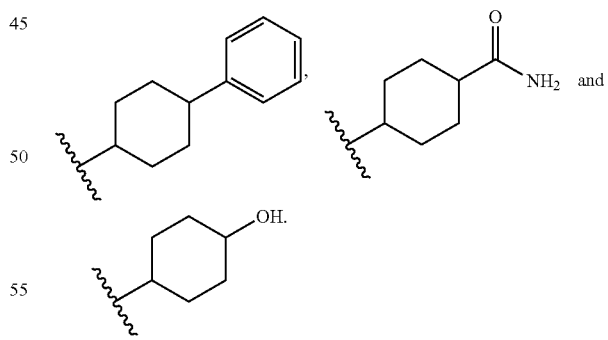

As used herein, the term "alkoxy" by itself or as part of another group refers to an optionally substituted alkyl, optionally substituted cycloalkyl, optionally substituted alkenyl, or optionally substituted alkynyl attached to a terminal oxygen atom. In one embodiment, the alkoxy group is chosen from a $C_{1-8}$ alkoxy group. In another embodiment, the alkoxy group is chosen from a $C_{1-8}$ alkyl attached to a terminal oxygen atom, e.g., methoxy, ethoxy, butoxy, and tert-butoxy.

As used herein, the term "alkenyl" by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

As used herein, the term "optionally substituted alkenyl" by itself or as part of another group means the alkenyl as defined above is either unsubstituted or substituted with one, two or three substituents independently selected from the group consisting of halo, nitro, cyano, hydroxyl, amino, (alkyl)amino, (dialkyl)amino, haloalkyl, (hydroxy)alkyl, (dihydroxy)alkyl, alkoxy, haloalkoxy, aryloxy, aralkyloxy, (alkyl)sulfanyl, carboxamido, sulfonamido, (alkyl)carbonyl, (aryl)carbonyl, (alkyl)sulfonyl, (aryl)sulfonyl, ureido, guanidino, carboxy, (carboxy)alkyl, alkyl, cycloalkyl, alkenyl, alkynyl, aryl, heteroaryl, heterocyclyl, amides, (alkyl)phosphates, nitrile, (alkyl)ethers, (alkyl)esters, and silyl, such as alkyl silyl.

As used herein, the term "alkynyl" by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

As used herein, the term "optionally substituted alkynyl" by itself or as part of another group means the alkynyl as defined above is either unsubstituted or substituted with one, two or three substituents independently selected from the group consisting of halo, nitro, cyano, hydroxyl, amino, alkylamino, dialkylamino, haloalkyl, (hydroxy)alkyl, (dihydroxy)alkyl, alkoxy, haloalkoxy, alkeneoxy, aryloxy, aralkyloxy, (alkyl)sulfanyl, carboxamido, sulfonamido, alkylcarbonyl, arylcarbonyl, alkylsulfonyl, arylsulfonyl, ureido, guanidino, carboxy, (carboxy)alkyl, alkyl, cycloalkyl, alkenyl, alkynyl, aryl, heteroaryl, heterocyclyl, amides, (alkyl) phosphates, nitrile, (alkyl)ethers, (alkyl)esters, and silyl, such as alkyl silyl.

As used herein, the term "aryl" by itself or as part of another group refers to a monocyclic or bicyclic aromatic ring system having from six to fourteen carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl.

As used herein, the term "optionally substituted aryl" by itself or as part of another group means that the aryl as defined above is either unsubstituted or substituted with one to five substituents independently selected from the group consisting of halo, nitro, cyano, hydroxyl, amino, alkylamino, dialkylamino, haloalkyl, (hydroxy)alkyl, (dihydroxy)alkyl, alkoxy, haloalkoxy, aryloxy, heteroaryloxy, aralkyloxy, alkylthio, carboxamido, sulfonamido, (alkyl) carbonyl, (aryl)carbonyl, (alkyl)sulfonyl, (aryl)sulfonyl, ureido, guanidino, carboxy, car-boxyalkyl, alkyl, cycloalkyl, alkenyl, alkynyl, aryl, heteroaryl, heterocyclo, (alkoxy)alkyl, (amino)alkyl, [(hydroxyl)alkyl]amino, [(alkyl)amino] alkyl, [(dialkyl)amino)alkyl, (cyano)alkyl, (carboxamido) alkyl, mercaptoalkyl, (heterocyclo)alkyl, (cycloalkylamino) alkyl, (halo($C_1$-$C_4$)alkoxy)alkyl, (heteroaryl)alkyl, amides, (alkyl)phosphates, nitrile, (alkyl)ethers, (alkyl)esters, and silyl, such as alkyl silyl. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-di-methoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Examples include:

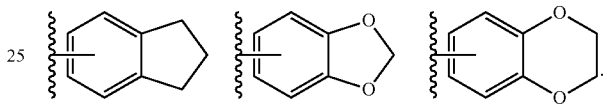

As used herein, the term "heteroaryl" or "heteroaromatic" refers to monocyclic and bicyclic aromatic ring systems having 5 to 14 ring atoms (i.e., $C_5$-$C_{14}$ heteroaryl) and 1, 2, 3, or 4 heteroatoms independently chosen from oxygen, nitrogen and sulfur. In one embodiment, the heteroaryl has three heteroatoms. In another embodiment, the heteroaryl has two heteroatoms. In another embodiment, the heteroaryl has one heteroatom. In one embodiment, the heteroaryl is a $C_5$ heteroaryl. In another embodiment, the heteroaryl is a $C_6$ heteroaryl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Exemplary N-oxides include pyridyl N-oxide and the like.

As used herein, the term "optionally substituted heteroaryl" by itself or as part of another group means that the heteroaryl as defined above is either unsubstituted or substituted with one to four substituents, e.g., one or two substituents, independently selected from the group consisting of halo, nitro, cyano, hydroxy, amino, (alkyl)amino, (dialkyl)amino, haloalkyl, (hydroxy)alkyl, (dihydroxy)alkyl, alkoxy, haloalkoxy, aryloxy, aralkyloxy, alkylthio, carboxamido, sulfonamido, (alkyl)carbonyl, (aryl)carbonyl, (alkyl)sulfonyl, (aryl)sulfonyl, ureido, guanidino, carboxy, (carboxy)alkyl, alkyl, cycloalkyl, alkenyl, alkynyl, aryl, heteroaryl, heterocyclo, (alkoxy)alkyl, (amino)alkyl, [(hydroxyl)alkyl]amino, [(alkyl)amino]alkyl, [(dialkyl)amino]alkyl, (cyano)alkyl, (carboxamido)alkyl, mercaptoalkyl, (heterocyclo)alkyl, (heteroaryl)alkyl, and the like. In one embodiment, the optionally substituted heteroaryl has one substituent.

For the purpose of the present invention, compounds comprising a stereocenter are considered to encompass and disclose both enantiomers, unless specifically indicated. In case that a compound comprises more than one stereocenter, all diastereomers as well as enantiomers are considered to be encompassed and disclosed, unless specifically indicated. If reference is made to a composition or mixture comprising a compound according to the present invention, it is understood that the compound can be present either as enantiomerically and/or diastereomerically pure compound or as a mixture of enantiomers and/or diastereomers, for example as a racemic mixture of the L or D-enantiomers of the amino acid residues as defined hereinafter. The same applies with regard to the synthesis of the compounds of the present invention, which compounds can be obtained either as enantiomerically and/or diastereomerically pure compounds or as a mixture of enantiomers and/or diastereomers, for example as a racemic mixture of the L or D-enantiomers of the amino acid residue as defined hereinafter.

As discussed above, the present invention relates to a compound of formula (I) or a salt thereof wherein

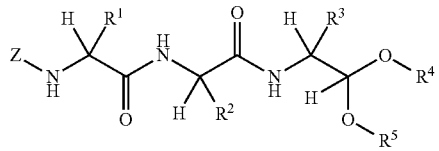

$R^1$, $R^2$ and $R^3$ are each independently selected from the group consisting of hydrogen, optionally substituted $C_{1-8}$ alkyl, optionally substituted $C_{2-6}$ alkenyl, optionally substituted $C_{1-8}$ alkoxy, optionally substituted 3- to 12-membered cycloalkyl, and optionally substituted 6- to 10-membered aryl; or wherein each $R^1$, $R^2$ and $R^3$ is independently selected as —$(CH_2)_3$— which is also attached to the nitrogen atom of —NH—C(H)— so that —N—C(H)$R^{1,2\ or\ 3}$— forms a 5-membered heterocyclic ring;

$R^4$ and $R^5$ are each independently selected from the group consisting of hydrogen, optionally substituted $C_{1-8}$ alkyl, optionally substituted $C_{2-6}$ alkenyl, optionally substituted $C_{1-8}$ alkoxy, optionally substituted $C_{1-4}$ acyl, optionally substituted $C_{1-8}$ alkyl phenyl (e.g. benzyl), and optionally substituted 6- to 10-membered aryl; or wherein $R^4$ and $R^5$ are joined to form an optionally substituted 5- or 6-membered ring;

Z is selected from hydrogen, an N-terminal protection group, and one or more amino acid residues optionally comprising an N-terminal protection group.

Preferably, each of $R^1$ and $R^2$ is a group such that NH—CHR$^1$—CO and NH—CHR$^2$—CO is an L or D-amino acid residue. L or D-amino acid residues include the L or D-form of glycine (Gly), alanine (Ala), valine (Val), leucine (Leu), isoleucine (Ile), methionine (Met), proline (Pro), phenylalanine (Phe), tryptophane (Trp), serine (Ser), threonine (Thr), aspartic acid (Asp), glutamine (Gln), tyrosine (Tyr), cysteine (Cys), lysine (Lys), arginine (Arg), histidine (His), asparagine (Asn), glutamic acid (Glu), m-tyrosine, 3,4-dihydroxyphenylalanine, norvaline (Nva) and norleucine (Nle).

Preferably, $R^1$ is a group such that NH—CHR$^1$—CO is an L or D-amino acid residue of Gly, Ala, Val, Leu, Ile, Met, Pro, Phe, Trp, Ser, Thr, Asp, Gln, Tyr, Cys, Lys, Arg, His, Asn, Glu, m-tyrosine, 3,4-dihydroxyphenylalanine, Nva, or Nle. More preferably, $R^1$ is a group such that NH—CHR$^1$—CO is an L or D-amino acid residue of Ala, Val, Gly, Arg, Leu, Phe, Ile, His or Thr. Even more preferably, $R^1$ is a group such that NH—CHR$^1$—CO is an L or D-amino acid residue of Ala, Val, Gly, Arg, Leu, Ile or His.

Preferably, $R^2$ is a group such that NH—CHR$^2$—CO is an L or D-amino acid residue of Gly, Ala, Val, Leu, Ile, Met, Pro, Phe, Trp, Ser, Thr, Asp, Gln, Tyr, Cys, Lys, Arg, His, Asn, Glu, m-tyrosine, 3,4-dihydroxyphenylalanine, Nva, or Nle. More preferably, $R^2$ is a group such that NH—CHR$^2$—CO is an L or D-amino acid residue of Ala, Cys, Gly, Pro, Ser, Thr, Val, Nva or Nle. Even more preferably, $R^2$ is a group such that NH—CHR$^2$—CO is an L or D-amino acid residue of Ala, Gly, Pro or Val.

In one embodiment, each of $R^1$ and $R^2$ is a group such that NH—CHR$^1$—CO and NH—CHR$^2$—CO is an L or D-amino acid residue of Gly, Ala, Val, Leu, Ile, Met, Pro, Phe, Trp, Ser, Thr, Asp, Gln, Tyr, Cys, Lys, Arg, His, Asn, Glu, m-tyrosine, 3,4-dihydroxyphenylalanine, Nva or Nle.

In one embodiment $R^1$ is a group such that NH—CHR$^1$—CO is an L or D-amino acid residue of Ala, Val, Gly, Arg, Leu, Ile or His and $R^2$ is a group such that NH—CHR$^2$—CO is an L or D-amino acid residue of Ala. In one embodiment $R^1$ is a group such that NH—CHR$^1$—CO is an L or D-amino acid residue of Ala, Val, Gly, Arg, Leu, Ile or His and $R^2$ is a group such that NH—CHR$^2$—CO is an L or D-amino acid residue of Gly. In one embodiment $R^1$ is a group such that NH—CHR$^1$—CO is an L or D-amino acid residue of Ala, Val, Gly, Arg, Leu, Ile or His and $R^2$ is a group such that NH—CHR$^2$—CO is an L or D-amino acid residue of Pro. In one embodiment $R^1$ is a group such that NH—CHR$^1$—CO is an L or D-amino acid residue of Ala, Val, Gly, Arg, Leu, Ile or His and $R^2$ is a group such that NH—CHR$^2$—CO is an L or D-amino acid residue of Val.

In one embodiment $R^1$ is a group such that NH—CHR$^1$—CO is an L or D-amino acid residue of Ala and $R^2$ is a group such that NH—CHR$^2$—CO is an L or D-amino acid residue of Ala, Gly, Pro or Val. In one embodiment $R^1$ is a group such that NH—CHR$^1$—CO is an L or D-amino acid residue of Val and $R^2$ is a group such that NH—CHR$^2$—CO is an L or D-amino acid residue of Ala, Gly, Pro or Val. In one embodiment $R^1$ is a group such that NH—CHR$^1$—CO is an L or D-amino acid residue of Gly and $R^2$ is a group such that NH—CHR$^2$—CO is an L or D-amino acid residue of Ala, Gly, Pro or Val. In one embodiment $R^1$ is a group such that NH—CHR$^1$—CO is an L or D-amino acid residue of Arg and $R^2$ is a group such that NH—CHR$^2$—CO is an L or D-amino acid residue of Ala, Gly, Pro or Val. In one embodiment $R^1$ is a group such that NH—CHR$^1$—CO is an L or D-amino acid residue of Leu and $R^2$ is a group such that NH—CHR$^2$—CO is an L or D-amino acid residue of Ala, Gly, Pro or Val. In one embodiment $R^1$ is a group such that NH—CHR$^1$—CO is an L or D-amino acid residue of Ile and $R^2$ is a group such that NH—CHR$^2$—CO is an L or D-amino acid residue of Ala, Gly, Pro or Val. In one embodiment $R^1$ is a group such that NH—CHR$^1$—CO is an L or D-amino acid residue of His and $R^2$ is a group such that NH—$CHR^2$—CO is an L or D-amino acid residue of Ala, Gly, Pro or Val.

In one embodiment $R^1$ is a group such that NH—$CHR^1$—CO is an L or D-amino acid residue of Gly and $R^2$ is a group such that NH—$CHR^2$—CO is an L or D-amino acid residue of Ala. In one embodiment $R^1$ is a group such that NH—$CHR^1$—CO is an L or D-amino acid residue of Val and $R^2$ is a group such that NH—$CHR^2$—CO is an L or D-amino acid residue of Ala. In one embodiment $R^1$ is a group such that NH—$CHR^1$—CO is an L or D-amino acid residue of Arg and $R^2$ is a group such that NH—$CHR^2$—CO is an L or D-amino acid residue of Ala. In one embodiment $R^1$ is a group such that NH—$CHR^1$—CO is an L or D-amino acid residue of Gly and $R^2$ is a group such that NH—$CHR^2$—CO is an L or D-amino acid residue of Gly. In one embodiment $R^1$ is a group such that NH—$CHR^1$—CO is an L or D-amino acid residue of Arg and $R^2$ is a group such that NH—$CHR^2$—CO is an L or D-amino acid residue of Val. In one embodiment $R^1$ is a group such that NH—$CHR^1$—CO is an L or D-amino acid residue of Leu and $R^2$ is a group such that NH—$CHR^2$—CO is an L or D-amino acid residue of Val. In one embodiment $R^1$ is a group such that NH—$CHR^1$—CO is an L or D-amino acid residue of Ala and $R^2$ is a group such that NH—$CHR^2$—CO is an L or D-amino acid residue of Val. In one embodiment $R^1$ is a group such that NH—$CHR^1$—CO is an L or D-amino acid residue of His and $R^2$ is a group such that NH—$CHR^2$—CO is an L or D-amino acid residue of Ala. In one embodiment $R^1$ is a group such that NH—$CHR^1$—CO is an L or D-amino acid residue of He and $R^2$ is a group such that NH—$CHR^2$—CO is an L or D-amino acid residue of Pro. In one embodiment $R^1$ is a group such that NH—$CHR^1$—CO is an L or D-amino acid residue of He and $R^2$ is a group such that NH—$CHR^2$—CO is an L or D-amino acid residue of Gly.

In one embodiment, $R^3$ is a group selected from optionally substituted $C_{1-8}$ alkyl, such as $CH_2Si(CH_3)_3$, $C_{1-8}$ alkylphosphates such as $(CH_2)_nPO(OR)_2$, alkylnitriles such as $CH_2CN$, $C_{1-8}$ alkylsulfones such as $CH_2SO_2R$, $C_{1-8}$ alkylethers such as $(CH_2)_nOR$, $C_{1-8}$ alkylesters such as $CH_2CO_2R$, and $C_{1-8}$ alkylamides; optionally substituted $C_{1-8}$ alkoxy, optionally substituted 3- to 12-membered cycloalkyl, such as cyclohexylmethyl; and optionally substituted 6- to 10-membered aryl, wherein R is independently selected from the group consisting of hydrogen, optionally substituted $C_{1-8}$ alkyl, optionally substituted $C_{1-8}$ alkoxy, optionally substituted 3- to 12-membered cycloalkyl, optionally substituted 6- to 10-membered aryl, and optionally substituted 6- to 10-membered heteroaryl and n is an integer from 1 to 8, i.e. 1, 2, 3, 4, 5, 6, 7 or 8.

Preferably, $R^3$ is a group such that NH—$CHR^3$—CO is an L or D-amino acid residue of Tyr, m-tyrosine, 3,4-dihydroxyphenylalanine, Phe, Val, Ala, Met, Nva, Leu, He or Nle or other non-natural amino acids carrying alkyl groups. More preferably, $R^3$ is a group such that NH—$CHR^3$—CO is an L or D-amino acid residue of Tyr, Phe, Val, Ala or Leu.

In one embodiment, $R^2$ and $R^3$ is a group such that NH—$CHR^1$—CO, NH—$CHR^2$—CO and NH—$CHR^3$—CO each is an L or D-amino acid residue of Gly, Ala, Val, Leu, He, Met, Pro, Phe, Trp, Ser, Thr, Asp, Gln, Tyr, Cys, Lys, Arg, His, Asn, Glu, m-tyrosine, 3,4-dihydroxyphenylalanine, Nva or Nle.

In a preferred embodiment, $R^1$ and $R^2$ is a group such that NH—$CHR^1$—CO and NH—$CHR^2$—CO each is an L or D-amino acid residue of Ala, Cys, Gly, Pro, Ser, Thr, Val, Nva or Nle, and $R^3$ is a group such that NH—$CHR^3$—CO is an L or D-amino acid residue of Tyr, m-tyrosine, 3,4-dihydroxyphenylalanine, Phe, Val, Ala, Met, Nva, Leu, He or Nle.

In a preferred embodiment, $R^1$ is a group such that NH—$CHR^1$—CO is an L or D-amino acid residue of Gly or Val, $R^2$ is a group such that NH—$CHR^2$—CO is an L or D-amino acid residue of Ala, and $R^3$ is a group such that NH—$CHR^3$—CO is an L or D-amino acid residue of Tyr, Ala, or Leu.

In a particularly preferred embodiment, $R^1$ is a group such that NH—$CHR^1$—CO is an L or D-amino acid residue of Val, $R^2$ is a group such that NH—$CHR^2$—CO is an L or D-amino acid residue of Ala, and $R^3$ is a group such that NH—$CHR^3$—CO is an L or D-amino acid residue of Leu.

In another particularly preferred embodiment, $R^1$ is a group such that NH—$CHR^1$—CO is an L or D-amino acid residue of Gly, $R^2$ is a group such that NH—$CHR^2$—CO is an L or D-amino acid residue of Ala, and $R^3$ is a group such that NH—$CHR^3$—CO is an L or D-amino acid residue of Tyr.

In another particularly preferred embodiment, $R^1$ is a group such that NH—$CHR^1$—CO is an L or D-amino acid residue of Val, $R^2$ is a group such that NH—$CHR^2$—CO is an L or D-amino acid residue of Ala, and $R^3$ is a group such that NH—$CHR^3$—CO is an L or D-amino acid residue of Ala.

In a particularly preferred embodiment, $R^1$ is a group such that NH—$CHR^1$—CO is an L or D-amino acid residue of Val, $R^2$ is a group such that NH—$CHR^2$—CO is an L or D-amino acid residue of Ala, and $R^3$ is a group such that NH—$CHR^3$—CO is an L or D-amino acid residue of Norleucine.

In a particularly preferred embodiment, $R^1$ is a group such that NH—$CHR^1$—CO is an L or D-amino acid residue of Val, $R^2$ is a group such that NH—$CHR^2$—CO is an L or D-amino acid residue of Ala, and $R^3$ is a group such that NH—$CHR^3$—CO is an L or D-amino acid residue of Norvaline.

In one embodiment, Wand Ware each independently selected from hydrogen, methyl, ethyl, i-propyl, n-propyl, i-butyl, s-butyl, n-butyl, i-pentyl, 2-pentyl, 3-pentyl, neopentyl, cyclopentyl, cyclohexyl, and benzyl.

Preferably, $R^4$ and $R^5$ are each independently selected from methyl, ethyl, isopropyl, 2-butyl or 3-pentyl. More preferably, $R^4$ and $R^5$ are both methyl, ethyl, isopropyl, 2-butyl or 3-pentyl.

In another embodiment, Wand Ware joined to form an optionally substituted 5- to 12-membered ring. Examples of the resulting ring are substituted or unsubstituted dioxolanes, dioxanes, trioxanes. Preferably, the resulting ring is 1,3-dioxolane, 4-methyl-1,3-dioxolane, 4-hydroxymethyl-1,3-dioxolane 4,4-dimethyl-1,3-dioxolane, 4,5-dimethyl-1,3-dioxolane, 4,4,5-trimethyl-1,3-dioxolane, 4,4,5,5-tetramethyl-1,3-dioxolane, substituted or unsubstituted 1,3-dioxane, 1,3,5-trioxane.

Z is selected from hydrogen, an N-terminal protection group, and one or more amino acid residues optionally comprising an N-terminal protection group. Preferably, Z is an N-terminal protection group.

The N-terminal protection group may be selected from formyl, acetyl (Ac), benzoyl (Bz), trifluoroacetyl, fluorenylmethyloxycarbonyl (Fmoc), methoxysuccinyl, aromatic and aliphatic urethane protecting groups, benzyloxycarbonyl (Cbz), tert-butyloxycarbonyl (Boc), adaman-tyloxycarbonyl, p-methoxybenzyl carbonyl (MOZ), benzyl (Bn), p-methoxybenzyl (PMB) or p-methoxyphenyl (PMP), methoxycarbonyl (Moc); methoxyacetyl (Mac); methyl carbamate, a methylamino carbonyl/methyl urea group, tityl (Trt), 3,5-dimethoxyphenylisoproxycarbonyl (Ddz), 2-(4-biphenyl)isopropoxycarbonyl (Bpoc), 2-nitrophenylsulfenyl (Nps), 2-(4-nitrophenylsulfonyl)ethoxycarbonyl (Nsc), 1,1-dioxobenzo[b]thiophene-2-ylmethyloxycarbonyl (Bsmoc), (1,1-dioxonaphtho[1,2-b]thiophene-2-yl)methyloxycarbonyl (α-Nsmoc), 1-(4,4-dimethyl-2,6-dioxocyclohex-1-ylidene)-3-methylbutyl (ivDde), 2,7-di-tert-butyl-Fmoc (Fmoc*), 2-fluoro-Fmoc (Fmoc(2F)), 2-monoisooctyl-Fmoc (mio-Fmoc) and 2,7-diisooctyl-Fmoc (dio-Fmoc), tetrachlorophthaloyl (TCP), 2-phenyl(methyl)sulfonio)ethyloxycarbonyl tetrafluoroborate (Pms), ethanesulfonylethoxycarbonyl (Esc), 2-(4-sulfophenylsulfonyl)ethoxycarbonyl (Sps), allyloxycarbonyl (Alloc), o-nitrobenzenesulfonyl (oNBS), 2,4-dinitrobenzenesulfonyl (dNBS), Benzothiazole-2-sulfonyl (Bts), 2,2,2-trichloroethyloxycarbonyl (Troc), dithiasuccinoyl (Dts), p-nitrobenzyloxycarbonyl (pNZ), α-Azidoacids, Propargyloxycarbonyl (Poc), o-Nitrobenzyloxycarbonyl (oNZ), 4-Nitroveratryloxycarbonyl (NVOC), 2-(2-Nitrophenyl)propyloxycarbonyl (NPPOC), 2-(3,4-Methylenedioxy-6-nitrophenyl)propyloxycarbonyl (MNPPOC), 9-(4-Bromophenyl)-9-fluorenyl (BrPhF), Azidomethyloxycarbonyl (Azoc), Hexafluoroacetone (HFA), 2-Chlorobenzyloxycarbonyl (CI-Z), Trifluoroacetyl (tfa), 2-(Methylsulfonyl)ethoxycarbonyl (Msc), Tetrachlorophthaloyl (TCP), Phenyldisulphanylethyloxycarbonyl (Phdec), 2-Pyridyldisulphanylethyloxycarbonyl (Pydec), or 4-Methyltrityl (Mtt).

If Z is one or more amino acid residue(s) comprising an N-terminal protection group, the N-terminal protection group is preferably a small aliphatic group, e.g., formyl, acetyl, fluorenylmethyloxycarbonyl (Fmoc), tert-butyloxycarbonyl (Boc), methoxycarbonyl (Moc); methoxyacetyl (Mac); methyl carbamate or a methylamino carbonyl/methyl urea group. In the case of a tripeptide, the N-terminal protection group is preferably a bulky aromatic group such as benzoyl (Bz), benzyloxycarbonyl (Cbz), p-methoxybenzyl carbonyl (MOZ), benzyl (Bn), p-methoxybenzyl (PMB) or p-methoxyphenyl (PMP).

Further suitable N-terminal protection groups are described in Greene's Protective Groups in Organic Synthesis, Fifth Edition by Peter G. M. Wuts, published in 2014 by John Wiley & Sons, Inc and in Isidro-Llobet et al., Amino Acid-Protecting Groups, Chem. Rev. 2009 109(6), 2455-2504.

Preferably, the N-terminal protection group is selected from benzyloxycarbonyl (Cbz), p-methoxybenzyl carbonyl (MOZ), benzyl (Bn), benzoyl (Bz), p-methoxybenzyl (PMB), p-methoxyphenyl (PMP), formyl, acetyl (Ac), methyloxy, alkoxycarbonyl, methoxycarbonyl, fluorenylmethyloxycarbonyl (Fmoc), or tert-butyloxycarbonyl (Boc).

As discussed above, the present invention further relates to the use of the compound according to formula (I) for stabilizing an enzyme.

In one embodiment, the enzyme is a hydrolase. Hydrolases are a class of enzymes that is commonly used as biochemical catalysts that utilize water to break a chemical bond. In a preferred embodiment, the enzyme is selected from a lipase, protease, cutinase, amylase, carbohydrase, cellulase, pectinase, pectate lyase, mannanase, arabinase, galactanase, xylanase, oxidase, laccase, and peroxidase. Preferred hydrolases include esterases, such as nucleases, phosphodiesterases, lipases, and phosphatases; proteases, such as serine proteases; and glycoside hydrolases, such as cellulases and amylases.

In a preferred embodiment, the enzyme is a protease or a lipase.

Proteases (also known as proteinases or peptidases) hydrolyze the peptide bond between amino acid residues in a polypeptide chain. Proteases may be specific and limited to one or more recognition sites within a protein, or they may be nonspecific, digesting proteins into individual amino acids.

Proteases are members of class EC 3.4. Proteases include aminopeptidases (EC 3.4.11), dipeptidases (EC 3.4.13), dipeptidyl-peptidases and tripeptidyl-peptidases (EC 3.4.14), peptidyl-dipeptidases (EC 3.4.15), serine-type carboxypeptidases (EC 3.4.16), metallocarboxypeptidases (EC 3.4.17), cysteine-type carboxypeptidases (EC 3.4.18), omega peptidases (EC 3.4.19), serine endopeptidases (EC 3.4.21), cysteine endopeptidases (EC 3.4.22), aspartic endopeptidases (EC 3.4.23), metallo-endopeptidases (EC 3.4.24), threonine endopeptidases (EC 3.4.25), endopeptidases of unknown catalytic mechanism (EC 3.4.99).

Commercially available protease enzymes include but are not limited to LAVERGY™ Pro (BASF); ALCALASER®, BLAZER®, DURALASE™, DURAZYM™, RELASE®, RELASE® ULTRA, SAVINASE®, SAVINASE® ULTRA, PRIMASE®, POLARZYME®, KANNASE®, LIQUANASE®, LIQUANASE® ULTRA, OVOZYME®, CORONASE®, CORONASE® ULTRA, NEUTRASE®, EVERLASE® AND ESPERASE® (Novozymes A/S), those sold under the tradename MAXATASE®, MAXACAL®, MAXAPEM®, PURAFECT®, PURA-FECT® PRIME, PURAFECT MA®, PURAFECT OX®, PURAFECT OXP®, PURAMAX®, PROPERASE®, FN2®, FN3®, FN4®, EXCELLASE®, ERASER®, ULTIMASE®, OPTICLEAN®, EFFECTENZ®, PREFERENZ® AND O PTIMASE® (Danisco/DuPont), AXAPEM™ (Gist-Brocases N.V.), Bacillus lentus Alkaline Protease, and KAP (Bacillus alkalophilus subtilisin) from Kao.

Proteases can be classified by three criteria: the reaction catalyzed, the chemical nature of the catalytic site, and their evolutionary relationships. Endopeptidases cleave the target protein internally. Exopeptidases remove single amino acids from either the amino- or carboxyterminal end of a protein. Exopeptidases are divided into carboxypeptidases or aminopeptidases depending on whether they digest proteins from the carboxy- or amino-terminus, respectively.

Proteases are also classified based on their catalytic site architecture. In that regard, proteases can be classified into seven broad groups comprising serine proteases, cysteine proteases, threonine proteases, aspartic proteases, glutamic proteases, metalloproteases, and asparagine peptide lyases. Serine proteases have a serine in their active site that covalently attaches to one of the protein fragments as an enzymatic intermediate. This class includes the chymotrypsin family (chymotrypsin, trypsin, and elastase) and the subtilisin family. Cysteine proteases have a similar mechanism as serine proteases, but use cysteine rather than serine. They include plant proteases (papain from papaya, and bromelain from pineapple) as well as mammalian proteases such as calpains. Aspartic proteases have two essential aspartic acid residues that are close together in the active site although far apart in the protein sequence. This family includes the digestive enzymes pepsin and chymosin. Metalloproteases use metal ion cofactors to facilitate protein digestion and include thermolysin. Threonine proteases have threonine in the active site.

At least one protease may be selected from serine proteases (EC 3.4.21). Serine proteases or serine peptidases (EC 3.4.21) are characterized by having a serine in the catalytically active site, which forms a covalent adduct with the substrate during the catalytic reaction. A serine protease may be selected from the group consisting of chymotrypsin (e.g., EC 3.4.21.1), elastase (e.g., EC 3.4.21.36), elastase (e.g., EC 3.4.21.37 or EC 3.4.21.71), granzyme (e.g., EC 3.4.21.78 or EC 3.4.21.79), kallikrein (e.g., EC 3.4.21.34, EC 3.4.21.35, EC 3.4.21.118, or EC 3.4.21.119,) plasmin (e.g., EC 3.4.21.7), trypsin (e.g., EC 3.4.21.4), thrombin (e.g., EC 3.4.21.5,) and subtilisin (also known as subtilopeptidase, e.g., EC 3.4.21.62), the latter hereinafter also being referred to as "subtilisin".

A sub-group of the serine proteases tentatively designated subtilases has been proposed by Siezen et al. (1991), Protein Eng. 4:719-737 and Siezen et al. (1997), Protein Science 6:501-523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997), Protein Science 6:501-523.

The subtilases may be divided into 6 sub-divisions, i.e. the subtilisin family, thermitase family, the proteinase K family, the lantibiotic peptidase family, the kexin family and the pyrolysin family.

A subgroup of the subtilases are the subtilisins which are serine proteases from the family S8 as defined by the MEROPS database (merops.sanger.ac.uk). Peptidase family S8 contains the serine endopeptidase subtilisin and its homologues.

Prominent members of family S8, subfamily A are: Subtilisin Carlsberg (S08.001), Subtilisin lentus (S08.003), Thermitase (S08.007), Subtilisin BPN' (S08.034), Subtilisin DY (S08.037), Alkaline peptidase (S08.038), Subtilisin ALP 1 (S08.045), Subtilisin sendai (S08.098) and Alkaline elastase YaB (S08.157).

Parent proteases of the subtilisin type (EC 3.4.21.62) and variants may be bacterial proteases. Said bacterial protease may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* protease, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* protease. A review of this family is provided, for example, in "Subtilases: Subtilisin-like Proteases" by R. Siezen, pages 75-95 in "Subtilisin enzymes", edited by R. Bott and C. Betzel, New York, 1996.

At least one protease may be selected from the following: subtilisin from *Bacillus amyloliquefaciens* BPN' (described by Vasantha et al. (1984) J. Bacteriol. 159, p. 811-819 and J A Wells et al. (1983) in Nucleic Acids Research, 11, p. 7911-7925); subtilisin from *Bacillus licheniformis* (subtilisin Carlsberg; disclosed in E L Smith et al. (1968) J. Biol Chem, 243, pp. 2184-2191, and Jacobs et al. (1985) in Nucl. Acids Res, 13, p. 8913-8926); subtilisin PB92 (original sequence of the alkaline protease PB92 is described in EP 283075 A2); subtilisin 147 and/or 309 (Esperase®, Savinase®, respectively) as disclosed in WO 89/06279; subtilisin from *Bacillus lentus* as disclosed in WO 91/02792, such as from *Bacillus lentus* DSM 5483 or the variants of *Bacillus lentus* DSM 5483 as described in WO 95/23221; subtilisin from *Bacillus alcalophilus* (DSM 11233) disclosed in DE 10064983; subtilisin from *Bacillus gibsonii* (DSM 14391) as disclosed in WO 2003/054184; subtilisin from *Bacillus* sp. (DSM 14390) disclosed in WO 2003/056017; subtilisin from *Bacillus* sp. (DSM 14392) disclosed in WO 2003/055974; subtilisin from *Bacillus gibsonii* (DSM 14393) disclosed in WO 2003/054184; subtilisin having SEQ ID Na: 4 as described in WO 2005/063974; subtilisin having SEQ ID Na: 4 as described in WO 2005/103244; subtilisin having SEQ ID Na: 7 as described in WO 2005/103244; and subtilisin having SEQ ID Na: 2 as described in application DE 102005028295.4.

At least one subtilisin may be subtilisin 309 (which might be called Savinase® herein) as disclosed as sequence a) in Table I of WO 89/06279 or a variant which is at least 80% identical thereto and has proteolytic activity.

Proteases are known as comprising the variants described in: WO 92/19729, WO 95/23221, WO 96/34946, WO 98/20115, WO 98/20116, WO 99/11768, WO 01/44452, WO 02/088340, WO 03/006602, WO 2004/03186, WO 2004/041979, WO 2007/006305, WO 2011/036263, WO 2011/036264, and WO 2011/072099. Suitable examples comprise especially protease variants of subtilisin protease derived from SEQ ID NO:22 as described in EP 1921147 (with amino acid substitutions in one or more of the following positions: 3, 4, 9, 15, 24, 27, 33, 36, 57, 68, 76, 77, 87, 95, 96, 97, 98, 99, 100, 101, 102, 103, 104, 106, 118, 120, 123, 128, 129, 130, 131, 154, 160, 167, 170, 194, 195, 199, 205, 206, 217, 218, 222, 224, 232, 235, 236, 245, 248, 252 and 274 which have proteolytic activity. In addition, a subtilisin protease is not mutated at positions Asp32, His64 and Ser221.

At least one subtilisin may have SEQ ID NO:22 as described in EP 1921147, or is a variant thereof which is at least 80%, at least 90%, at least 95% or at least 98% identical SEQ ID NO:22 as described in EP 1921147 and has proteolytic activity. In one embodiment, a subtilisin is at least 80%, at least 90%, at least 95% or at least 98% identical to SEQ ID NO:22 as described in EP 1921147 and is characterized by having amino acid glutamic acid (E), or aspartic acid (D), or asparagine (N), or glutamine (Q), or alanine (A), or glycine (G), or serine (S) at position 101 (according to BPN' numbering) and has proteolytic activity. In one embodiment, subtilisin is at least 80%, at least 90%, at least 95% or at least 98% identical to SEQ ID NO:22 as described in EP 1921147 and is characterized by having amino acid glutamic acid (E) or aspartic acid (D), preferably glutamic acid (E), at position 101 (according to BPN' numbering) and has proteolytic activity. Such a subtilisin variant may comprise an amino acid substitution at position 101, such as R101E or R101D, alone or in combination with one or more substitutions at positions 3, 4, 9, 15, 24, 27, 33, 36, 57, 68, 76, 77, 87, 95, 96, 97, 98, 99, 100, 101, 102, 103, 104, 106, 118, 120, 123, 128, 129, 130, 131, 154, 160, 167, 170, 194, 195, 199, 205, 206, 217, 218, 222, 224, 232, 235, 236, 245, 248, 252 and/or 274 (according to BPN' numbering) and has proteolytic activity. In a preferred embodiment, the subtilisin protease is identical to SEQ ID NO:22 as described in EP 1921147 except that the protease is characterized by having amino acid glutamic acid (E) at position 101 (according to BPN' numbering). In one embodiment, said protease comprises one or more further substitutions: (a) threonine at position 3 (3T), (b) isoleucine at position 4 (4I), (c) alanine, threonine or arginine at position 63 (63A, 63T, or 63R), (d) aspartic acid or glutamic acid at position 156 (156D or 156E), (e) proline at position 194 (194P), (f) methionine at position 199 (199M), (g) isoleucine at position 205 (205I), (h) aspartic acid, glutamic acid or glycine at position 217

(217D, 217E or 217G), (i) combinations of two or more amino acids according to (a) to (h).

A suitable subtilisin may be at least 80% identical to SEQ ID NO:22 as described in EP 1921147 and is characterized by comprising one amino acid (according to (a)-(h)) or combinations according to (i) together with the amino acid 101E, 101D, 101N, 101Q, 101A, 101G, or 101S (according to BPN' numbering) and has proteolytic activity.

In one embodiment, a subtilisin is at least 80% identical to SEQ ID NO:22 as described in EP 1921147 and is characterized by comprising the mutation (according to BPN' numbering) R101E, or S3T+V4I+V205I, or S3T+V4I+R101E+V205I or S3T+V4I+V199M+V205I+L217D, and has proteolytic activity. If secretion of these proteases into the fermentation medium is desired the use of the signal peptide of the AprE protein from *Bacillus subtilis* is preferred.

In another embodiment, the subtilisin comprises an amino acid sequence having at least 80% identity to SEQ ID NO:22 as described in EP 1921147 and being further characterized by comprising S3T+V4I+S9R+A15T+V68A+D99S+R101S+A103S+I104V+N218D (according to the BPN' numbering) and has proteolytic activity.

A subtilisin may have an amino acid sequence being at least 80% identical to SEQ ID NO:22 as described in EP 1921147 and being further characterized by comprising R101E, and one or more substitutions selected from the group consisting of S156D, L262E, Q137H, S3T, R45E,D, Q, P55N, T58W,Y,L, Q59D,M,N,T, G61 D,R, S87E, G97S, A98D,E,R, S106A,W, N117E, H120V,D,K,N, S125M, P129D, E136Q, S144W, S161T, S163A,G, Y171 L, A172S, N185Q, V199M, Y209W, M222Q, N238H, V244T, N261T,D and L262N,Q,D (as described in WO 2016/096711 and according to the BPN' numbering), and has proteolytic activity.

In one embodiment the subtilisin has the amino acid sequence according to SEQ ID NO:1 of the present sequence listing.

The subtilisin may be of animal, vegetable or microbial origin, including chemically or genetically modified mutants (protein engineered variants). Examples of subtilisins are those derived from *Bacillus*, e.g. subtilisin Novo, subtilisin Carlsberg, subtilisin BPN', subtilisin 309, subtilisin 147 and subtilisin 168 (described in WO 89/06279) and Protease PD138 (WO 93/18140). Further examples of subtilisins are described in WO 98/020115, WO 01/44452, WO 01/58275, WO 01/58276, WO 03/006602 and WO 04/099401. Other examples of subtilisins are the variants described in WO 92/19729, WO 98/20115, WO 98/20116, WO 98/34946, WO 2011/036263 and mixtures of proteases.

Examples of commercially available subtilisins include Kannase™, Everlase™, Relase™, Esperase™, Alcalase™ Durazym™, Savinase™, Ovozyme™, Liquanase™, Coronase™, Polarzyme™, Pyrase™, Pancreatic Trypsin NOVO (PIN), Bio-Feed™ Pro and Clear-Lens™ Pro; Blaze (all available from Novozymes A/S, Bagsvaerd, Denmark). Other commercially available subtilisins include Ronozyme™ Pro, Maxatase™, Maxacal™, Maxapem™, Opticlean™ Properase™, Purafast™ Purafect™ Purafect Ox™, Purafact Prime™, Excellase™, FN2™, FN3™ and FN4™ (available from Genencor International Inc., Gist-Brocades, BASF, or DSM). Other examples are Primase™ and Duralase™. Blap R, Blap S and Blap X available from Henkel.

In another embodiment, the enzyme is a lipase. Lipases or triacylglycerol hydrolases are a class of enzymes that catalyze the hydrolysis of lipids.

Suitable lipases include those of bacterial or fungal origin. Chemically modified or protein engineered mutants are included. Examples include lipase from *Thermomyces*, e.g. from *T. lanuginosus* (previously named *Humicola lanuginosa*) as described in EP 258 068 and EP 305 216, a *Pseudomonas* lipase,e.g. from *P. alcaligenes* or *P. pseudo alcaligenes* (EP 218 272), *P. cepacia* (EP 331 376), *P. stutzeri*(GB 1,372,034), *P. fluorescens, Pseudomonas* sp. strain SD 705 (WO 95/06720 and WO 96/27002), *P. wisconsinensis* (WO 96/12012), a *Bacillus* lipase,e.g. from *B. subtilis* (Dartois et al., 1993, Biochemica et Biophysica Acta, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079, WO 97/07202, WO 00/060063, WO 2007/087508 and WO 2009/109500.

Preferred commercially available lipase enzymes include Lipolase™, Lipolase Ultra™, and Lipex™; Lecitase™, Lipolex™; Lipoclean™ Lipoprime™ (Novozymes A/S). Other commercially available lipases include Lumafast (Genencor Int Inc); Lipomax (Gist-Bro-cades/Genencor Int Inc) and *Bacillus* sp lipase from Solvay.

In another embodiment, the enzyme is an amylase.

Suitable amylases (α and/or β) include those of bacterial or fungal origin. Chemically modified or protein engineered mutants are included. Amylases include, for example, α-amylases obtained from *Bacillus*, e.g. a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Stainzyme; Stainzyme Plus; Duramyl™, Termamyl™, Termamyl Ultra; Natalase, Fungamyl™ and BAN™ (Novozymes A/S), Rapidase™ and Purastar™ (from Genencor International Inc.).

Suitable cutinases include those of bacterial or fungal origin. Chemically modified or protein engineered mutants are included. Examples include cutinase from *Humicola*, e.g. *H. insolensas* described in WO 96/13580.

The pectate lyase may be a wild-type enzyme derived from *Bacillus*, particularly *B. licheniformis* or, *B. agaradhaerens*, or a variant derived of any of these, e.g. as described in U.S. Pat. No. 6,124,127, WO 99/027083, WO 99/027084, WO 2002/006442, WO 2002/092741, and WO 2003/095638. Commercially available pectate lyases include XPect, Pectawash and Pectaway (Novozymes A/S).

The mannanase may be an alkaline mannanase of Family 5 or 26. It may be a wild-type from *Bacillus* or *Humicola*, particularly *from B. agaradhaerens, B. licheniformis, B. halodurans, B. clausii*, or *H. insolens*. Suitable mannanases are described in WO 99/064619. A commercially available mannanase is Mannaway (Novozymes A/S).

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophile* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care bene-fits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/01544.

Commercially available cellulases are Celluzyme, Celluclean, Endolase, Carezyme, Renozyme, and whitezyme (Novozymes A/S) or Biotouch (AB Enzymes).

As discussed above, the present invention further relates a composition comprising a compound according to formula (I) and an enzyme, preferably a hydrolase, more preferably a protease and most preferably a subtilisin.

The composition can be provided in liquid or granular form. The composition may be added to a detergent composition, which further comprises one or more surfactants. The detergent composition may, e.g. be a laundry detergent composition or a dishwashing detergent composition.

The liquid detergent composition is in a physical form, which is not solid (or gas). It may be a pourable liquid, a pourable gel or a non-pourable gel. It may be either isotropic or structured, preferably it is isotropic. It includes formulations useful for washing in automatic washing machines or for hand washing. The detergent composition contains at least one surfactant. The detergent composition may also include a builder.

The particulate detergent composition may be a granulate or powder, or a powder/granulate pressed to a tablet, briquette. The detergent composition may be in the form of a tablet, bar or pouch, including multi-compartment pouches. The detergent composition can be in the form of a powder, for example a free-flowing powder, such as an agglomerate, spray-dried powder, encapsulate, extrudate, needle, noodle, flake, or any combination thereof.

Pouches can be of any form, shape and material which is suitable for holding the composition, e.g. without allowing the release of the composition from the pouch prior to water contact. The pouch is made from water-soluble film, which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water-soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably, the level of polymer in the film for example PVA is at least about 60%. Preferred average molecular weight will typically be about 20,000 to about 150,000. Films can also be a blend compositions comprising hydrolytically degradable and water-soluble polymer blends such as polyactide and polyvinyl alcohol (known under the Trade reference M8630 as sold by Chris Craft In. Prod. Of Gary, Ind., US) plus plasticizers like glycerol, ethylene glycerol, Propylene glycol, sorbitol and mixtures thereof. The pouches can comprise a solid laundry cleaning composition or part components and/or a liquid cleaning composition or part components separated by the water-soluble film. The compartment for liquid components can be different in composition from compartments containing solids (see e.g. US 2009/0011970).

In one embodiment, the composition according to the present invention may be added to a detergent composition in an amount corresponding to 0.001-100 mg of protein, such as 0.01-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of detergent composition. In a composition such as a liquid or granular detergent, the amount of each enzyme (e.g. subtilisin and optionally a second or more enzymes) will typically be 0.04-80 µM (or µmol/kg), in particular 0.2-30 µM, especially 0.4-20 µM (generally 1-2000 mg/l or mg/kg, in particular 5-750 mg/l, especially 10-500 mg/l) calculated as pure enzyme protein. In a composition such as an enzyme concentrate the amount of each enzyme will typically be 0.01-20 mM, in particular 0.04-10 mM, especially 0.1-5 mM (generally 0.3-500 g/l, in particular 1-300 g/l, especially 3-150 g/l) calculated as pure enzyme protein.

The molar ratio of a compound according to formula (I) to the enzyme (e.g. subtilisin) is at least 1:1 or 1.5:1, and it is less than 1000:1, more preferred less than 500:1, even more preferred from 100:1 to 2:1 or from 20:1 to 2:1, or most preferred, the molar ratio is from 10:1 to 2:1.

In one embodiment, the composition comprises at least one further enzyme which is also called the second enzyme. In a preferred embodiment, the at least one further enzyme is selected from a lipase, protease, cutinase, amylase, carbohydrase, cellulase, pectinase, pectate lyase, mannanase, arabinase, galactanase, xylanase, oxidase, laccase, peroxidase and combinations thereof. Preferably, the second enzyme is an enzyme as described herein. The composition may contain one or more additional proteases, if the first enzyme is a protease. The composition may contain one, two or more non-subtilisin enzymes. The composition may contain one or more additional subtilisins, if the first enzyme is a subtilisin.

As described above, the detergent composition may comprise one or more surfactants, which may be anionic and/or cationic and/or non-ionic and/or semi-polar and/or zwitterionic, or a mixture thereof. In one embodiment, the detergent composition includes a mixture of one or more non-ionic surfactants and one or more anionic surfactants.

The surfactant(s) is typically present from about 0.1% to 60% by weight, such as from about 1% to about 40%, or from about 3% to about 20%, or from about 3% to about 10%. The surfactant(s) is chosen based on the desired cleaning application, and includes any conventional surfactant(s) known in the art. Any surfactant known in the art for use in detergents may be utilized.

Examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diyl-bis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates, including sodium lauryl ether sulfate (SLES), soaps or fatty acids; secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent composition will usually contain from about 1% to about 40% by weight, such as from about 5% to about 30%, including from about 5% to about 15%, or from about 20% to about 25% of an anionic surfactant.

Examples of non-ionic surfactants include alcohol ethoxylates (AE or AEO), alcohol propoxylates, propoxylated fatty alcohols (PEA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamide (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent composition will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%.

The detergent composition may contain about 0-65% by weight of a builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Examples of builders that can be included are in particular silicates, aluminum silicates (in particular zeolites), carbonates, salts of organic di- and polycarboxylic acids and mixtures of these substances. Non-limiting examples of builders include zeolites, diphosphates (pyrophosphates), triphosphates such as sodium triphosphate (STP or STPP), nitrilotriacetic acid, ethylenediaminetetraacetic acid (EDTA), diethylenetriaminepentaacetic acid, alkyl- or alkenylsuccinic acid, carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof.

The builder may be a strong builder such as methyl glycine diacetic acid ("MGDA") or N,N-Dicarboxymethyl glutamic acid tetrasodium salt (GLDA); it may be a medium builder such as sodium tri-poly-phosphate (STPP), or it may be a weak builder such as sodium citrate.

Organic builders that can be present in the detergent composition are for example the polycarboxylic acids that can be used in the form of their sodium salts, polycarboxylic acids being understood to be carboxylic acids bearing more than one acid function. These are for example citric acid, adipic acid, succinic acid, glutaric acid, malic acid, tartaric acid, maleic acid, fumaric acid, sugar acids, aminocarboxylic acids, nitrilotriacetic acid (NTA), methyl glycine diacetic acid (MGDA) and derivatives and mixtures thereof. Preferred salts are the salts of polycarboxylic acids such as citric acid, adipic acid, succinic acid, glutaric acid, tartaric acid, sugar acids and mixtures thereof.

Polymeric polycarboxylates are also suitable as builders. These are for example the alkali metal salts of polyacrylic acid or polymethacrylic acid, for example those having a relative molar mass of 600 to 750,000 g/mol.

Suitable polymers are in particular polyacrylates, which preferably have a molar mass of 1000 to 15,000 g/mol. Of this group, owing to their superior solubility, preference can in turn be given to the short-chain polyacrylates having molar masses of 1000 to 10,000 g/mol and particularly preferably of 1000 to 5000 g/mol.

Also suitable are copolymeric polycarboxylates, in particular those of acrylic acid with methacrylic acid and of acrylic acid or methacrylic acid with maleic acid. To improve their solubility the polymers can also contain allyl sulfonic acids, such as all yloxybenzenesulfonic acid and methallyl sulfonic acid, as monomers.

However, soluble builders, such as for example citric acid, or acrylic polymers having a molar mass of 1000 to 5000 g/mol are preferably used.

Within the meaning of this application the molar masses specified for the polymeric polycarboxylates are weight-average molar masses $M_w$ of the individual acid form, which were determined in principle by gel permeation chromatography (GPC) using a UV detector. The measurement was carried out against an external polyacrylic acid standard, which because of its structural affinity to the polymers under investigation delivers realistic molar mass values. These figures differ markedly from the molar mass values obtained using polystyrene sulfonic acids as the standard. The molar masses measured against polystyrene sulfonic acids are generally significantly higher than the molar masses given in this publication.

Such organic builder substances can be included if desired in amounts of up to 40 wt.-%, in particular up to 25 wt.-% and preferably from 1 wt.-% to 8 wt.-%. Amounts close to the cited upper limit are preferably used in paste-form or liquid, in particular water-containing, detergent compositions.

In the case that the compositions according to the invention are provided in liquid form, they contain preferably water as the main solvent. Non-aqueous solvents can also or additionally be used. Suitable non-aqueous solvents encompass mono- or polyhydric alcohols, alkanolamines or glycol ethers, provided they are miscible with water in the specified concentration range. The solvents are preferably selected from ethanol, n-propanol, isopropanol, butanols, glycol, propanediol, butanediol, glycerol, diglycol, propyl diglycol, butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ether, propylene glycol ethyl ether, propylene glycol propyl ether, dipropylene glycol monomethyl ether, dipropylene glycol monoethyl ether, diisopropylene glycol monomethyl ether, diisopropylene glycol monoethyl ether, methoxytriglycol, ethoxytriglycol, butoxytriglycol, 1-butoxyethoxy-2-propanol, 3-methyl-3-methoxybutanol, propylene glycol t-butyl ether, di-n-octyl ether and mixtures of these solvents. It is however preferable for the composition to contain a polyol as the non-aqueous solvent. The polyol can in particular encompass glycerol, 1,2-propanediol, 1,3-propanediol, ethylene glycol, diethylene glycol and/or dipropylene glycol. The composition preferably contains in particular a mixture of a polyol and a monohydric alcohol. Non-aqueous solvents can be used in amounts of between 0.5 and 15 wt.-%, but preferably below 12 wt.-%.

To set a desired pH that is not established automatically by mixing the other components, the composition can contain system-compatible and environmentally compatible acids, in particular citric acid, acetic acid, tartaric acid, malic acid, lactic acid, glycolic acid, succinic acid, glutaric acid and/or adipic acid, but also mineral acids, in particular sulfuric acid, or bases, in particular ammonium or alkali hydroxides. Such pH regulators are included in the agents in amounts preferably not exceeding 20 wt.-%, in particular from 1.2 wt.-% to 17 wt.-%.

A composition according to the invention can furthermore contain one or more water-soluble salts, which serve the purpose of viscosity adjustment for example. They can be inorganic and/or organic salts. Inorganic salts that can be used are preferably selected from the group comprising colorless water-soluble halides, sulfates, sulfites, carbonates, hydrogen carbonates, nitrates, nitrites, phosphates and/or oxides of alkali metals, alkaline-earth metals, aluminum and/or transition metals; ammonium salts can also be used. Halides and sulfates of alkali metals are particularly preferred; the inorganic salt is therefore preferably selected from the group comprising sodium chloride, potassium chloride, sodium sulfate, potassium sulfate and mixtures thereof. Organic salts that can be used are for example colorless water-soluble alkali metal, alkaline-earth metal, ammonium, aluminum and/or transition metal salts of carboxylic acids. The salts are preferably selected from the group comprising formate, acetate, propionate, citrate, malate, tartrate, succinate, malonate, oxalate, lactate and mixtures thereof.

The composition can contain one or more thickening agents for thickening purposes. The thickening agent is preferably selected from the group comprising xanthan gum, guar gum, carrageenan, agar agar, gellan, pectin, carob seed meal and mixtures thereof. These compounds are effective thickening agents even in the presence of inorganic salts. The thickening agent additionally stabilizes the continuous, low-surfactant phase and prevents a macroscopic phase separation.

The composition may comprise further enzyme inhibitors or stabilizers. Examples of such enzyme inhibitors or stabilizers are boric acid and boronic acids. Examples of boronic acids are alkyl boronic acids such as methylboronic acid, butylboronic acid, and 2-cyclohexylethylboronic acid; and aryl boronic acids such as phenylboronic acid, 4-methoxyphenylboronic acid, 3,5-dichlorophenylboronic acid, and 4-formylphenylboronic acid (4-FPBA).

The present invention is further directed to a method of preparing the composition according to the invention.

In one embodiment, the method comprises the step of mixing the enzyme, preferably protease, the compound of formula (I) and optionally one or more surfactants.

The present invention is further directed to a cleaning agent comprising the compound according to formula (I) or the composition according to the invention.

The present invention is further directed to a method of preparing a compound of formula (I) or a salt thereof. The method comprises the following steps:

a) providing a compound according to formula

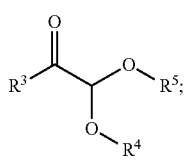

b) converting the compound of step a) to

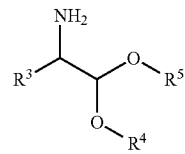

or the corresponding salt thereof having the formula

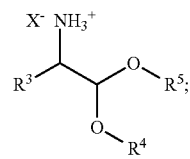

c) reacting the compound or the corresponding salt thereof obtained in step b) with

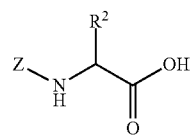

to obtain

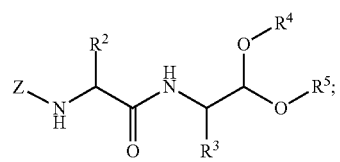

d) optionally, converting the compound obtained in step c) to

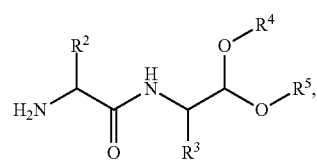

if Z in the compound of step c) is not hydrogen;

e) reacting the compound obtained in step c) or d) with

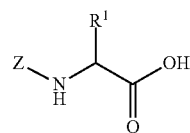

to obtain a compound according to formula (I)

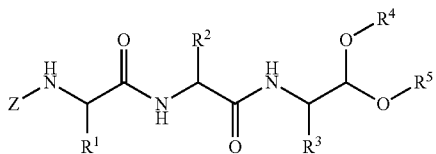

or a salt thereof.

X is selected from F, Cl, Br and I and $R^1$ to $R^5$ and Z are defined as hereinabove.

The following examples are provided for illustrative purposes. It is thus understood that the examples are not to be construed as limiting. The skilled person will clearly be able to envisage further modifications of the principles laid out herein.

EXAMPLES

A. Synthesis Examples

Example 1: Preparation of Z-Val-Ala-Ala-(OMe)$_2$ a)

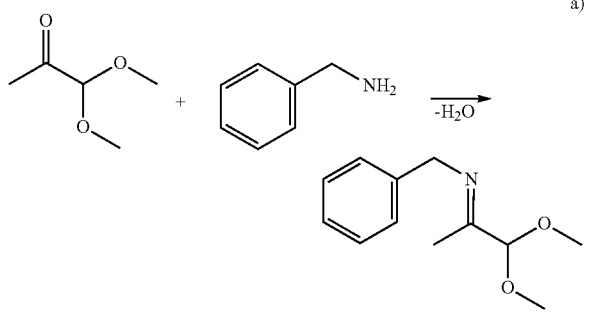

To a solution of 50 ml (49 g, 0.46 mol) benzylamine in 250 ml heptane in a 20° C. water bath was added 64.5 ml (63 g, 0.53 mol) pyruvic aldehyde dimethylacetal. Temperature rose to ~30° C. 20 g anhydrous MgSO$_4$ was added and the suspension was allowed to stir for 16 h at 20° C. The suspension was concentrated before the unreacted starting materials were removed under high vacuum at 35° C. 81.6 g (86%) of a colorless oil was obtained. $^1$H NMR (CDCl$_3$) 7.22-7.38 (m, 5), 4.573 (br s, 2), 4.567 (s, 1), 3.45 (s, 6) and 1.55 (s, 3) ppm.

81.6 g (0.39 mol) of the above compound was dissolved in 430 ml methanol and cooled to 5° C. in an ice-salt bath. 17.04 g NaBH$_4$ (0.45 mol) was added to the clear solution in ~15 portions. The first 5 portions caused a rise in temperature to 10-12° C. and much H$_2$ evolved. The resulting suspension was allowed to stir overnight and warm to RT. The light yellow solution formed was concentrated in vacuo. 150 ml toluene and 200 ml water were added to the residue. The organic phase was separated and aqueous phase extracted with 100 ml toluene. The combined organic phases were dried over MgSO$_4$ and concentrated in vacuo to give 77.5 g (94%) of a pale yellow oil. $^1$H NMR (CDCl$_3$) 7.43-7.17 (m, 5), 4.17 (d, 1), 3.82 (dd, 2), 3.41 (s, 3), 3.38 (s, 3), 2.86 (pentet, 1), 1.76 (br s, 1), and 1.13 (d, 3) ppm.

c)

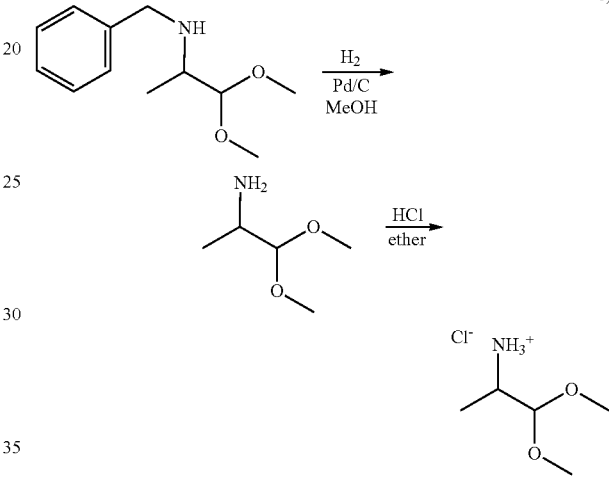

76.7 g (0.37 mol) of the above compound was hydrogenated in 430 ml methanol with 7.5 g 10% Pd/C and 3 bar H$_2$ for 26 h. The solution was then filtered and concentrated and dissolved in 300 ml ether. The ethereal solution was cooled to 4° C. and 11.0 g gaseous HCl were introduced over 1.5 h. At the end of the addition, the suspension was allowed to warm to RT and stir for 3 h. The suspension was filtered, washed with 2×50 ml ether, then dried under high vacuum to afford 42.5 g (0.27 mol, 74%) of a white solid. $^1$H NMR (D$_2$O) 4.70 (br s, 3), 4.46 (d, 1), 3.49 (s, 3), 3.46 (s, 3), 3.44 (dq, 1), and 1.25 (d, 3) ppm.

d)

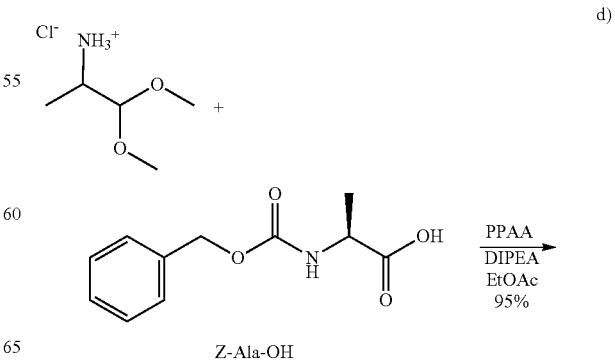

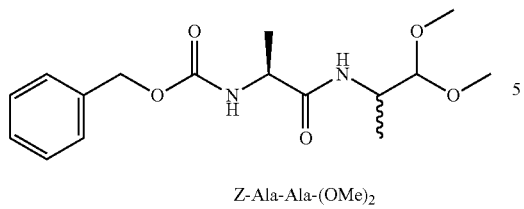

Z-Ala-Ala-(OMe)₂

To a suspension of 7.68 g (49 mmol) of the above compound in 100 ml ethyl acetate in a water bath at RT was added 26.6 ml (19.4 g, 150 mmol) diisopropylethylamine via syringe. Temperature decreased slightly and the suspension became lighter. 11.67 g (52 mmol) Z-Ala-OH was added as a solid followed by 35.2 ml 50% (59 mmol) propylphosphonic acid anhydride (PPAA) over 30 min by means of a syringe pump. Temperature decreased slightly. The resulting pale yellow suspension was allowed to stir at RT for 5 h. The Reaction mixture was poured into 100 ml sat'd NaHCO₃. Organic phase was separated and washed with 50 ml water, 50 ml brine, then dried over MgSO₄ and concentrated in vacuo to give 14.85 g (93%) of an off-white solid. ¹HNMR (CDCl₃) 7.42-7.30 (m, 5), 6.19 (br s, 1), 5.49 (br s, 1), 5.12 (br s, 2), 4.30-4.08 (m, 3), 3.45-3.36 (4s, 6), 1.39 (d, 3) and 1.12 (br d, 3) ppm.

e)

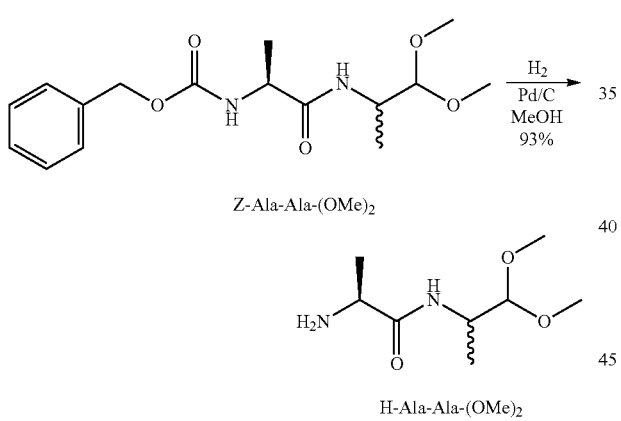

H-Ala-Ala-(OMe)₂

14.0 g (43 mmol) of the above compound was hydrogenated in 140 ml methanol with 1.5 g 10% Pd/C and 3 bar H₂ for 17 h. The solution was then filtered and concentrated in vacuo to provide 7.63 g (64 mmol, 93%) of pale yellow oil. ¹HNMR (CDCl₃) 7.34 (m, 1), 4.24-4.07 (m, 2), 3.49 (dq, 1), 3.45-3.42 (4s, 6), 1.50 (br s, 2), 1.34 (dd, 3), and 1.14 (dd, 3) ppm.

To a solution of 4.06 g (21.3 mmol) of the above compound in 75 ml methyl-t-butylether at RT was added 7.6 ml (5.65 g, 44 mmol) diisopropylethylamine via syringe. Temperature decreased slightly and the suspension became lighter. 5.68 g (22.6 mmol) Z-Val-OH was added as a solid followed by 15.3 ml 50% (26 mmol) propylphosphonic acid anhydride (PPAA) over 40 min by means of a syringe pump. The resulting suspension was allowed to stir overnight at RT. The suspension was treated with 100 ml sat'd NaHCO₃ and filtered washing the solid with water and methyl-t-butylether. Drying under high vacuum gave 7.65 g (85%) of a fluffy white solid. ¹HNMR (CDCl₃) 7.47-7.29 (m, 5), 6.58 (br s, 1), 6.22 (br s, 1), 5.14 (m, 2), 4.48 (pentet, 1), 4.24-4.10 (m, 2), 4.05 (br t, 1), 3.46-3.38 (4s, 6), 2.14 (septet, 1), 1.39 (d, 3), 1.18-1.08 (m, 3) and 1.03-0.87 (3d, 6) ppm.

Example 2: Preparation of Z-Val-Ala-Leu-(OMe)₂

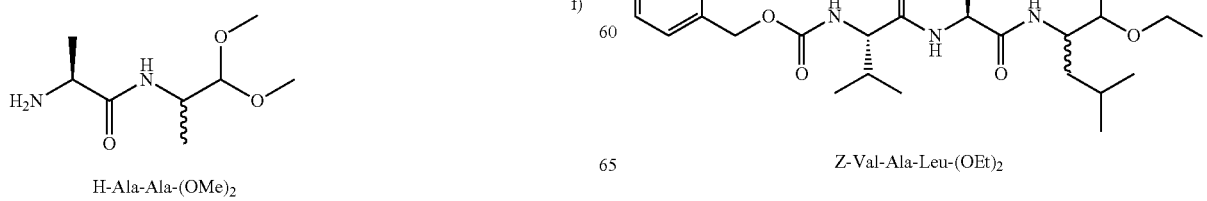

Z-Val-Ala-Leu-(OMe)₂ was obtained via steps analogous to steps a) to 1) of Example 1.

Example 3: Preparation of Z-Val-Ala-Leu-(OEt)₂ f)

Z-Val-Ala-Leu-(OEt)₂

Z-Val-Ala-Leu-(OEt)₂ was obtained via steps analogous to steps a) to f) of Example 1.

Example 4: Preparation of Z-Val-Ala-Nva-(OEt)₂

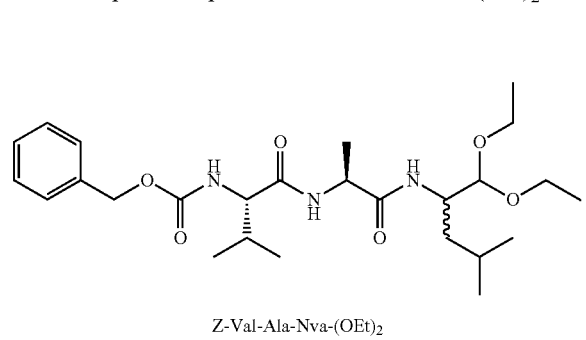

Z-Val-Ala-Nva-(OEt)₂

Z-Val-Ala-Nva-(OEt)₂ was obtained via steps analogous to steps a) to f) of Example 1.

Example 5: Preparation of Z-Val-Ala-Phe-(OMe)₂

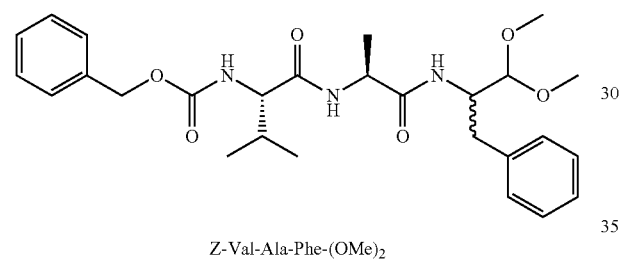

Z-Val-Ala-Phe-(OMe)₂

Z-Val-Ala-Phe-(OMe)₂ was obtained via steps analogous to steps a) to f) of Example 1.

Example 6: Preparation of Z-Val-Ala-Nva-(O-iPr)₂

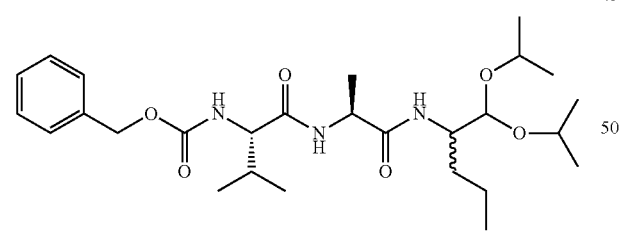

Z-Val-Ala-Nva(O-iPr)₂

A mixture of 6.77 g (15 mmol) Cbz-Val-Ala-Nva-(OE0₂ from Example 6 above and 0.38 g (1.5 mmol) pyridinium tosylate in 60 ml isopropanol was heated under reflux overnight. After cooling, the thick suspension was filtered, the solid washed with 20 ml cold isopropanol. Recrystallization of the solid in isopropanol gave 1.06 (14%) of a white solid. ¹H NMR (CDCl₃) 7.45-7.30 (m, 5), 6.65-6.39 (m, 1), 6.02-5.79 (m, 1), 5.43-5.26 (br d, 1), 5.14 (m, 2), 4.56-4.38 (m, 2), 4.12-3.92 (m, 2), 3.92-3.39 (m, 2), 2.13 (septet, 1) and 1.72-0.84 (multiple m, 28) ppm.

Example 7: Preparation of Z-Val-Ala-Leu-(O-iPr)₂

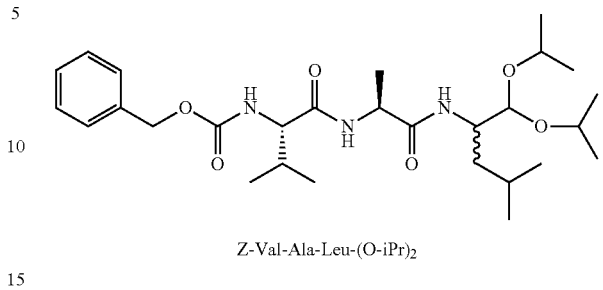

Z-Val-Ala-Leu-(O-iPr)₂

Z-Val-Ala-Leu-(O-iPr)₂ was obtained analogous to Example 6.

Example 8: Preparation of Z-Val-Ala-Leu-(O-iBu)₂

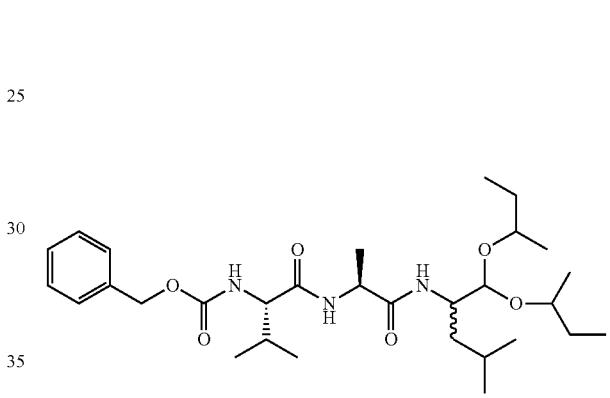

Z-Val-Ala-Leu-(O-iBu)₂

Z-Val-Ala-Leu-(O-iBu)₂ was obtained was obtained analogous to Example 6.

Example 9: Preparation of Z-Val-Ala-Phe-(O-iPr)₂

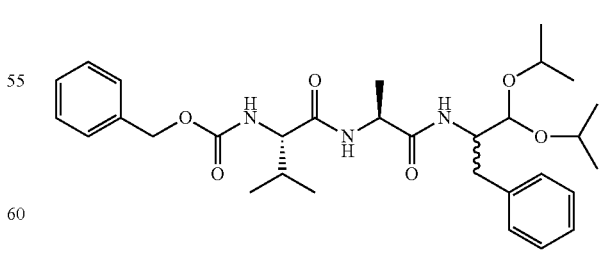

Z-Val-Ala-Phe-(O-iPr)₂

Z-Val-Ala-Phe-(O-Pr)₂ was obtained analogous to Example 6.

Example 10: Preparation of Z-Val-Ala-Leu-(O-3-pentyl)₂

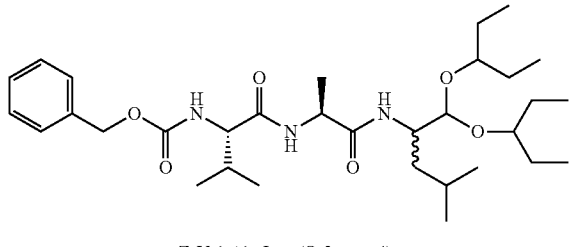

Z-Val-Ala-Leu-(O-3-pentyl)₂

Z-Val-Ala-Leu-(O-3-pentyl)₂ was obtained analogous to Example 6.

Example 11: Preparation of Z-Val-Ala-Phe-(O-neopentyl)₂

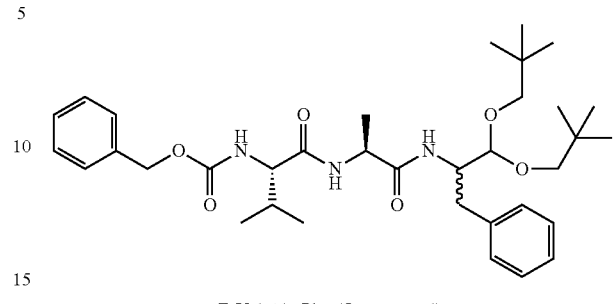

Z-Val-Ala-Phe-(O-neopentyl)₂

Z-Val-Ala-Phe-(O-neopentyl)₂ was obtained was obtained analogous to Example 6.

B. Storage and Proteases Stability

To assess the ability of synthesized peptides to stabilize a protease storage trials were performed using a subtilisin according to SEQ ID NO:1 being the BLAP WT and being characterized by comprising the mutation (according to BPN' numbering) R101E.

For the storage trials compositions as depicted in Table 1 with the ingredients given in w/w were prepared:

|  | Formulation 1 | Formulation 2 | Formulation 3 | Formulation 4 |
|---|---|---|---|---|
| Protease BLAP R101E | 5% | 5% | 5% | 5% |
| Propylenglycol | 53% | 53% | 53% | 53% |
| CaCl2 | 0.3 | 0.3 | 0.3 | 0.3 |
| Stabilizer |  |  |  |  |
| (1) Cbz-Val-Ala-Ala-(OMe)2 (Example 1) (molecular weight: 377 g/mol) | x | X |  |  |
| (2) Cbz-Val-Ala-Ala-H (molecular weight 407 g/mol) |  |  | x | x |
| pH | 4.50 | 5.50 | 4.50 | 5.50 |
| H₂O | to 100% | to 100% | to 100% | to 100% | stabilizers were added in 10 fold molar excess over protease

The compositions were stored at a temperature of 30° for 31, 60 and 119 days and the residual protease activity after storage was analyzed by measuring the reactivity towards the peptidic substrate Suc-AAPF-pNA. Here pNA is cleaved from the substrate molecule at 30° C., pH 8.6 using 100 mM TRIS buffer. The rate of cleavage, directly proportional to the protease activity, can be determined by the increase of the yellow color of free pNA in the solution by measuring $OD_{405}$, the optical density at 405 nm.

In Table 2 the residual activity is given referenced to the initial value. It can be seen that the stabilizer according to the invention (Formulations 1 and 2) is superior over its reference molecule tested in formulations 3 and 4 under the two different pH conditions, i.e., pH 4.5 and pH 5.5.

|  | 0 days | 31 days | 60 days | 119 days |
|---|---|---|---|---|
| Formulation 1 | 100% | 103% | 105% | 108% |
| Formulation 2 | 100% | 101% | 100% | 95% |
| Formulation 3 | 100% | 88% | 71% | 42% |
| Formulation 4 | 100% | 56% | 28% | 10% |

The invention claimed is:

1. A compound of formula (I) or a salt thereof

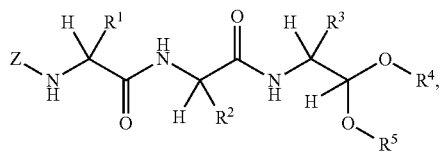

formula (I)

wherein:

$R^1$ is a group such that NH—$CHR^1$—CO is an L or D-amino acid residue of Gly or Val, $R^2$ is a group such that NH—$CHR^2$—CO is an L or D-amino acid residue of Ala, and $R^3$ is a group such that NH—$CHR^3$—CO is an L or D-amino acid residue of Tyr, Ala, or Leu;

$R^4$ and $R^5$ are each independently selected from the group consisting of hydrogen, optionally substituted $C_{1-8}$ alkyl, optionally substituted $C_{2-6}$ alkenyl, optionally substituted $C_{1-8}$ alkoxy, optionally substituted $C_{1-4}$ acyl, optionally substituted $C_{1-8}$ alkyl phenyl, and optionally substituted 6- to 10-membered aryl; or wherein $R^4$ and $R^5$ are joined to form an optionally substituted 5- to 12-membered ring; and Z is selected from hydrogen, an N-terminal protection group, or one or more amino acid residues optionally comprising an N-terminal protection group.

2. The compound of claim 1, wherein $R^4$ and $R^5$ are each independently selected from methyl (Me), ethyl (Et), iso-propyl (iPr) or isobutyl (iBu).

3. The compound of claim 2, wherein $R^4$ and $R^5$ are each independently selected from methyl or ethyl.

4. The compound of claim 1, wherein $R^4$ and $R^5$ are both methyl, ethyl, or isopropyl.

5. The compound of claim 1, wherein Z is an N-terminal protection group.

6. The compound of claim 5, wherein the N-terminal protection group is selected from benzyloxycarbonyl (Cbz), p-methoxybenzyl carbonyl (MOZ), benzyl (Bn), benzoyl (Bz), p-methoxybenzyl (PMB), p-methoxyphenyl (PMP), formyl, acetyl (Ac), methyloxy, alkoxycarbonyl, methoxycarbonyl (Moc), fluorenylmethyloxycarbonyl (Fmoc) or tert-butyloxycarbonyl (t-Boc).

7. The compound of claim 1, wherein the compound is selected from:
Cbz-Gly-Ala-Tyr-(OMe)$_2$,
Cbz-Gly-Ala-Tyr-(OEt)$_2$,
Ac-Gly-Ala-Tyr-(OMe)$_2$,
Ac-Gly-Ala-Tyr-(OEt)$_2$,
Cbz-Gly-Ala-Tyr-(OiPr)$_2$,
Cbz-Gly-Ala-Tyr-(OiBu)$_2$,
Ac-Gly-Ala-Tyr-(OiPr)$_2$,
Ac-Gly-Ala-Tyr-(OiBu)$_2$,
Bz-Gly-Ala-Tyr-(OMe)$_2$,
Bz-Gly-Ala-Tyr-(OEt)$_2$,
Fmoc-Gly-Ala-Tyr-(OMe)$_2$,
Fmoc-Gly-Ala-Tyr-(OEt)$_2$,
Bz-Gly-Ala-Tyr-(OiPr)$_2$,
Bz-Gly-Ala-Tyr-(OiBu)$_2$,
Fmoc-Gly-Ala-Tyr-(OiPr)$_2$,
Fmoc-Gly-Ala-Tyr-(OiBu)$_2$,
Cbz-Gly-Ala-Leu-(OMe)$_2$,
Cbz-Gly-Ala-Leu-(OEt)$_2$,
Ac-Gly-Ala-Leu-(OMe)$_2$,
Ac-Gly-Ala-Leu-(OEt)$_2$,
Cbz-Gly-Ala-Leu-(OiPr)$_2$,
Cbz-Gly-Ala-Leu-(OiBu)$_2$,
Ac-Gly-Ala-Leu-(OiPr)$_2$,
Ac-Gly-Ala-Leu-(OiBu)$_2$,
Bz-Gly-Ala-Leu-(OMe)$_2$,
Bz-Gly-Ala-Leu-(OEt)$_2$,
Fmoc-Gly-Ala-Leu-(OMe)$_2$,
Fmoc-Gly-Ala-Leu-(OEt)$_2$,
Bz-Gly-Ala-Leu-(OiPr)$_2$,
Bz-Gly-Ala-Leu-(OiBu)$_2$,
Fmoc-Gly-Ala-Leu-(OiPr)$_2$,
Fmoc-Gly-Ala-Leu-(OiBu)$_2$,
Cbz-Val-Ala-Leu-(OMe)$_2$,
Cbz-Val-Ala-Leu-(OEt)$_2$,
Ac-Val-Ala-Leu-(OMe)$_2$,
Ac-Val-Ala-Leu-(OEt)$_2$,
Cbz-Val-Ala-Leu-(OiPr)$_2$,
Cbz-Val-Ala-Leu-(OiBu)$_2$,
Ac-Val-Ala-Leu-(OiPr)$_2$,
Ac-Val-Ala-Leu-(OiBu)$_2$,
Bz-Val-Ala-Leu-(OMe)$_2$,
Bz-Val-Ala-Leu-(OEt)$_2$,
Fmoc-Val-Ala-Leu-(OMe)$_2$,
Fmoc-Val-Ala-Leu-(OEt)$_2$,
Bz-Val-Ala-Leu-(OiPr)$_2$,
Bz-Val-Ala-Leu-(OiBu)$_2$,
Fmoc-Val-Ala-Leu-(OiPr)$_2$,
Fmoc-Val-Ala-Leu-(OiBu)$_2$,
Cbz-Val-Ala-Ala-(OMe)$_2$,
Cbz-Val-Ala-Ala-(OEt)$_2$,
Ac-Val-Ala-Ala-(OMe)$_2$,
Ac-Val-Ala-Ala-(OEt)$_2$,
Cbz-Val-Ala-Ala-(OiPr)$_2$,
Cbz-Val-Ala-Ala-(OiBu)$_2$,
Ac-Val-Ala-Ala-(OiPr)$_2$,
Ac-Val-Ala-Ala-(OiBu)$_2$,
Bz-Val-Ala-Ala-(OMe)$_2$,
Bz-Val-Ala-Ala-(OEt)$_2$,
Fmoc-Val-Ala-Ala-(OMe)$_2$,
Fmoc-Val-Ala-Ala-(OEt)$_2$,
Bz-Val-Ala-Ala-(OiPr)$_2$,
Bz-Val-Ala-Ala-(OiBu)$_2$,
Fmoc-Val-Ala-Ala-(OiPr)$_2$, or
Fmoc-Val-Ala-Ala-(OiBu)$_2$; and wherein Cbz is benzyloxycarbonyl, Ac is acetyl, Bz is benzyl, and Fmoc is fluorenylmethyloxycarbonyl.

8. A composition comprising a compound according to claim 1 and an enzyme.

9. The composition according to claim 8, wherein the enzyme is a protease.

10. The composition according to claim 9, wherein the protease is a serine protease.

11. The composition according to claim 8, wherein the composition further comprises a surfactant.

12. The composition according to claim 8, wherein the composition is in liquid or granular form.

13. The composition according to claim 8, wherein the composition comprises at least two different enzymes.

14. A method of preparing a composition, wherein the method comprises mixing the compound according to claim 1 and an enzyme.

15. A detergent composition comprising the compound according to claim 1 and a surfactant.

16. A method of preparing a compound of formula (I) as defined in claim 1, wherein the method comprises:

a) providing a compound according to formula b) converting the compound of step a) to or the corresponding salt thereof having the formula

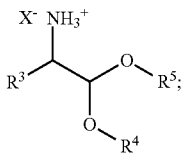

c) reacting the compound or the corresponding salt thereof obtained in step b) with

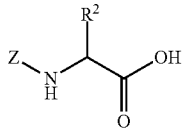

to obtain

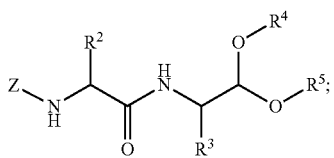

d) optionally, converting the compound obtained in step c) to

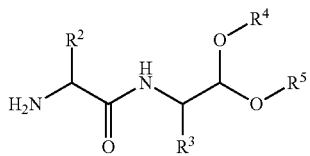

if Z is not hydrogen; and
e) reacting the compound obtained in step c) or d) with

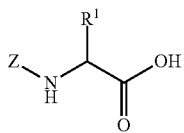

to obtain a compound according to formula (I)

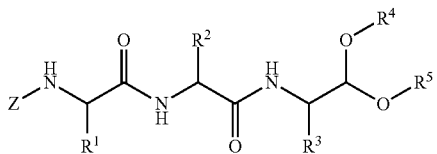

wherein X is selected from F, Cl, Br or I; and
wherein $R^1$ to $R^5$ and Z are defined as in claim 1.

17. A compound selected from:
Cbz-Gly-Ala-Val-(OMe)$_2$,
Cbz-Gly-Ala-Val-(OEt)$_2$,
Ac-Gly-Ala-Val-(OMe)$_2$,
Ac-Gly-Ala-Val-(OEt)$_2$,
Cbz-Gly-Ala-Val-(OiPr)$_2$,
Cbz-Gly-Ala-Val-(OiBu)$_2$,
Ac-Gly-Ala-Val-(OiPr)$_2$,
Ac-Gly-Ala-Val-(OiBu)$_2$,
Bz-Gly-Ala-Val-(OMe)$_2$,
Bz-Gly-Ala-Val-(OEt)$_2$,
Fmoc-Gly-Ala-Val-(OMe)$_2$,
Fmoc-Gly-Ala-Val-(OEt)$_2$,
Bz-Gly-Ala-Val-(OiPr)$_2$,
Bz-Gly-Ala-Val-(OiBu)$_2$,
Fmoc-Gly-Ala-Val-(OiPr)$_2$, or
Fmoc-Gly-Ala-Val-(OiBu)$_2$,
wherein Cbz is benzyloxycarbonyl, Ac is acetyl, Bz is benzyl, and Fmoc is fluorenylmethyloxycarbonyl.

18. A compound selected from:
Cbz-Val-Ala-Norvaline-(OMe)$_2$,
Cbz-Val-Ala-Norvaline-(OEt)$_2$,
Ac-Val-Ala-Norvaline-(OMe)$_2$,
Ac-Val-Ala-Norvaline-(OEt)$_2$,
Cbz-Val-Ala-Norvaline-(OiPr)$_2$,
Cbz-Val-Ala-Norvaline-(OiBu)$_2$,
Ac-Val-Ala-Norvaline-(OiPr)$_2$,
Ac-Val-Ala-Norvaline-(OiBu)$_2$,
Bz-Val-Ala-Norvaline-(OMe)$_2$,
Bz-Val-Ala-Norvaline-(OEt)$_2$,
Fmoc-Val-Ala-Norvaline-(OMe)$_2$,
Fmoc-Val-Ala-Norvaline-(OEt)$_2$,
Bz-Val-Ala-Norvaline-(OiPr)$_2$,
Bz-Val-Ala-Norvaline-(OiBu)$_2$,
Fmoc-Val-Ala-Norvaline-(OiPr)$_2$, or
Fmoc-Val-Ala-Norvaline-(OiBu)$_2$,
wherein Cbz is benzyloxycarbonyl, Ac is acetyl, Bz is benzyl, and Fmoc is fluorenylmethyloxycarbonyl.

19. A compound selected from:
Cbz-Val-Ala-Trimethylsilyl-Ala-(OMe)$_2$,
Cbz-Val-Ala-Trimethylsilyl-Ala-(OEt)$_2$,
Ac-Val-Ala-Trimethylsilyl-Ala-(OMe)$_2$,
Ac-Val-Ala-Trimethylsilyl-Ala-(OEt)$_2$,
Cbz-Val-Ala-Trimethylsilyl-Ala-(OiPr)$_2$,
Cbz-Val-Ala-Trimethylsilyl-Ala-(OiBu)$_2$,
Ac-Val-Ala-Trimethylsilyl-Ala-(OiPr)$_2$,
Ac-Val-Ala-Trimethylsilyl-Ala-(OiBu)$_2$,
Bz-Val-Ala-Trimethylsilyl-Ala-(OMe)$_2$,
Bz-Val-Ala-Trimethylsilyl-Ala-(OEt)$_2$,
Fmoc-Val-Ala-Trimethylsilyl-Ala-(OMe)$_2$,
Fmoc-Val-Ala-Trimethylsilyl-Ala-(OEt)$_2$,
Bz-Val-Ala-Trimethylsilyl-Ala-(OiPr)$_2$,
Bz-Val-Ala-Trimethylsilyl-Ala-(OiBu)$_2$,
Fmoc-Val-Ala-Trimethylsilyl-Ala-(OiPr)$_2$,
Fmoc-Val-Ala-Trimethylsilyl-Ala-(OiBu)$_2$,
Cbz-Val-Ala-Cyclohexyl-Ala-(OMe)$_2$,
Cbz-Val-Ala-Cyclohexyl-Ala-(OEt)$_2$,
Ac-Val-Ala-Cyclohexyl-Ala-(OMe)$_2$,
Ac-Val-Ala-Cyclohexyl-Ala-(OEt)$_2$,
Cbz-Val-Ala-Cyclohexyl-Ala-(OiPr)$_2$,
Cbz-Val-Ala-Cyclohexyl-Ala-(OiBu)$_2$,
Ac-Val-Ala-Cyclohexyl-Ala-(OiPr)$_2$,
Ac-Val-Ala-Cyclohexyl-Ala-(OiBu)$_2$,
Bz-Val-Ala-Cyclohexyl-Ala-(OMe)$_2$,
Bz-Val-Ala-Cyclohexyl-Ala-(OEt)$_2$,
Fmoc-Val-Ala-Cyclohexyl-Ala-(OMe)$_2$,
Fmoc-Val-Ala-Cyclohexyl-Ala-(OEt)$_2$,
Bz-Val-Ala-Cyclohexyl-Ala-(OiPr)$_2$,
Bz-Val-Ala-Cyclohexyl-Ala-(OiBu)$_2$,
Fmoc-Val-Ala-Cyclohexyl-Ala-(OiPr)$_2$, or Fmoc-Val-Ala-Cyclohexyl-Ala-(OiBu)$_2$,
wherein Cbz is benzyloxycarbonyl, Ac is acetyl, Bz is benzyl, and Fmoc is fluorenylmethyloxycarbonyl.

* * * * *